United States Patent
Pui et al.

(10) Patent No.: US 11,439,586 B2
(45) Date of Patent: Sep. 13, 2022

(54) INTRATUMOUR INJECTION FORMULATION

(71) Applicant: US Nano Food & Drug INC, New Castle, DE (US)

(72) Inventors: Hing Sang Pui, New Castle, DE (US); Yip Shu Pui, New Castle, DE (US)

(73) Assignee: US Nano Food & Drug INC, New Castle, DE (US)

( * ) Notice: Subject to any disclaimer, the term of this patent is extended or adjusted under 35 U.S.C. 154(b) by 0 days.

(21) Appl. No.: 16/544,146

(22) Filed: Aug. 19, 2019

(65) Prior Publication Data

US 2020/0113820 A1 Apr. 16, 2020

Related U.S. Application Data

(60) Provisional application No. 62/746,322, filed on Oct. 16, 2018.

(51) Int. Cl.
| | |
|---|---|
| A61K 9/00 | (2006.01) |
| A61K 31/337 | (2006.01) |
| A61K 31/4745 | (2006.01) |
| A61K 47/44 | (2017.01) |
| A61K 31/357 | (2006.01) |
| A61K 47/14 | (2017.01) |

(52) U.S. Cl.
CPC .......... *A61K 9/0019* (2013.01); *A61K 31/337* (2013.01); *A61K 31/357* (2013.01); *A61K 31/4745* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,573,781 A | 11/1996 | Brown et al. | |
| 5,681,846 A * | 10/1997 | Trissel | A61K 9/0019 514/449 |
| 5,698,582 A | 12/1997 | Bastart et al. | |
| 5,714,512 A | 2/1998 | Bastart et al. | |

(Continued)

FOREIGN PATENT DOCUMENTS

| | | |
|---|---|---|
| CN | 1923189 A | 3/2007 |
| CN | 102370645 B | 7/2014 |

(Continued)

OTHER PUBLICATIONS

Chen, T. et al. International Journal of Pharmaceutics 528 (2017) 127-132 (Year: 2017).*

(Continued)

*Primary Examiner* — Melissa S Mercier
(74) *Attorney, Agent, or Firm* — Davidson, Davidson & Kappel, LLC

(57) ABSTRACT

Formulations and uses of the formulations for treating a malignant mass in a mammal by administering an injectable formulation comprising a therapeutically effective amount of a chemotherapeutic agent dissolved or suspended in a biocompatible carrier directly into the malignant mass are disclosed. In certain preferred embodiments, the injectable formulation is a taxane (e.g. paclitaxel), a podophyllotoxin derivative (e.g., etoposide), or a camptothecin derivative (e.g., hydroxycamptothecin).

23 Claims, 1 Drawing Sheet

(56) References Cited

U.S. PATENT DOCUMENTS

| | | | |
|---|---|---|---|
| 6,979,456 B1* | 12/2005 | Parikh | A61K 9/1075 |
| | | | 424/422 |
| 7,923,536 B2* | 4/2011 | Desai | A61P 23/00 |
| | | | 977/911 |
| 8,710,013 B2* | 4/2014 | Demeule | A61P 35/00 |
| | | | 514/19.3 |
| 8,940,786 B2 | 1/2015 | Nabeta | |
| 9,308,195 B2 | 4/2016 | Nabeta | |
| 9,345,683 B2* | 5/2016 | Khamar | A61K 31/337 |
| 9,351,997 B2 | 5/2016 | Bender | |
| 9,636,406 B2 | 5/2017 | Bender | |
| 10,391,090 B2 | 8/2019 | Baltezor et al. | |
| 2002/0032171 A1 | 3/2002 | Chen et al. | |
| 2003/0099674 A1* | 5/2003 | Chen | A61K 47/44 |
| | | | 424/400 |
| 2003/0203033 A1 | 10/2003 | Dang et al. | |
| 2008/0090803 A1 | 4/2008 | Swindell et al. | |
| 2008/0319048 A1 | 12/2008 | Palepu et al. | |
| 2009/0118354 A1 | 5/2009 | Liu et al. | |
| 2010/0041744 A1 | 2/2010 | Chung et al. | |
| 2013/0150335 A1 | 6/2013 | Liu et al. | |
| 2017/0326232 A1 | 11/2017 | Guiducci et al. | |
| 2021/0113463 A1 | 4/2021 | Deschamps et al. | |

FOREIGN PATENT DOCUMENTS

| | | | |
|---|---|---|---|
| EP | 0674510 B1 * | 8/1998 | A61K 47/12 |
| EP | 1348430 A1 * | 10/2003 | A61K 31/335 |
| WO | WO 00/57852 | 10/2000 | |
| WO | WO 2010/083365 A1 | 7/2010 | |
| WO | WO 2019/016138 A1 | 1/2019 | |
| WO | WO 2020/035806 A1 | 2/2020 | |

OTHER PUBLICATIONS

Sellers, R. et al. Drug and Chemical Toxicology, 28:423-432, 2005 (Year: 2005).*

Wermuth, C. Drug Discovery Today vol. 11, Nos. 7/8, Apr. 2006, 348-354 (Year: 2006).*

Mead Johnson. Taxol Injection, Oncology Products, Feb. 10, 2000; [online], Retrieved from URL: https://www.accessdata.fda.gov/drugsatfda_docs/label/2000/20262S36LBL.PDF on Jan. 22, 2021. (Year: 2000).*

Xia et al. Chem. Pharm. Bull. 59(3) 321-326 (2011). (Year: 2011).*

Dordunoo, S. and Burt, H. International Journal of Pharmaceutics 133 (1996) 191-201. (Year: 1996).*

Yang et al. "Percutaneous intratumoral injection of gemcitabine plus cisplatin mixed with fibrin glue for advanced pancreatic carcinoma" Case Report; Journal List Medicine (Baltimore) v.96 (37); Sep. 2017.

Silas Inman "FDA Approves Alcohol-Free Docetaxel Formulation" from https://www.onclive.com/web-exclusives/fda-approves-alcohol-tree-docetaxel-formulation; Published Monday, Dec. 28, 2015.

Kevin Bullis "Nanospheres that target cancer cells and gradually release drugs could make treatment safer and more effective." MIT Technology Review, Single-Shot Chemo; Apr. 12, 2006.

Sato et al. "Direct Delivery of a Cytotoxic Anticancer Agent into the Metastatic Lymph Node Using Nano/Microbubbles and Ultrasound" PLOS One; from https://doi.org/10.1371/journal.pone.0123619; Published Apr. 21, 2015.

Sagiv-Barfi et al. "Eradication of spontaneous malignancy by local immunotherapy" Science Translational Medicine; vol. 10, Issue 426; Jan. 31, 2018.

Lexie Metzler "New IsoFlow Lateral Infusion Catheter Directly Targets Cancer Cells" from https://www.medicaldesignandoutsourcing.com. Published Oct. 14, 2016.

Matthew Contursi "United by chance, ASU alumni and a Silicon Valley entrepreneur team up to innovate cancer treatment" The State Press. Published Oct. 16, 2016.https://www.statepress.com/staff/matthew-contursl.

Andrew Octavian Sasmita "Why don't we directly inject drug into tumor?"; Internet Reference from https://wwwresearchgate.net/post/Why_dont_we_directly_inject_drug_into_tumor.

Bommareddy PK et al. "Intratumoral Approaches for the Treatment of Melanoma" Cancer J.; Jan./Feb. 2017; 23(1):40-47. Abstract only.

International Search Report and Written Opinion from corresponding PCT Application No. PCT/US19/47079 dated Nov. 6, 2019.

Tanaka K. et al. "Direct injection chemotherapy combined with arterial embolization in the treatment of liver cancers." Nihon Igaku Hoshasen Gakkai Zasshi; Mar. 25, 1992; 52(3); 408-10. Abstract Only.

Northwest Biotherapeutics "DCVax®—Direct Phase I/II for All Types of Inoperable Solid" https://nwbio.com/dcvax-direct-phase-iii-for-all-types-of-inoperable-solid-tumor-cancers/.

Northwest Biotherapeutics "A Phase I/II Clinical Trial Evaluating DCVaX-Direct, Autologous Activated Dendritic Cells for Intratumoral Injection, in Patients with Solid Tumors" Study Record Details; https://clinicaltrials.gov/ct2/show/NCT01882946?term=Northwest+Biotherapeutics&draw=2&rank=2; Posted on June 21, 2013.

Bhullar et al. "Intratumoral acetic acid injection eradicates human prostate cancer tumors in a murine model" World journal of urology; vol. 31; issue 2; pp. 331-337 (2012).

Ahnfelt et al. "Lipodol-based emulsions used for transarterial chemoembolization and drug delivery: Effects of composition on stability and product quality" Journal of Drug Science and Technology; vol. 53 (2019).

International Search Report and Written Opinion from corresponding PCT Application No. PCT/US2021/25006 dated Aug. 17, 2021.

Zhu et al. "Review on the Stability Mechanism and Application of Water-in-Oil Emulsions Encapsulating Various Additives" Comprehensive Reviews in Food Science and Food Safety. vol. 18; Issue 6; pp. 1660-16752 (2019).

* cited by examiner

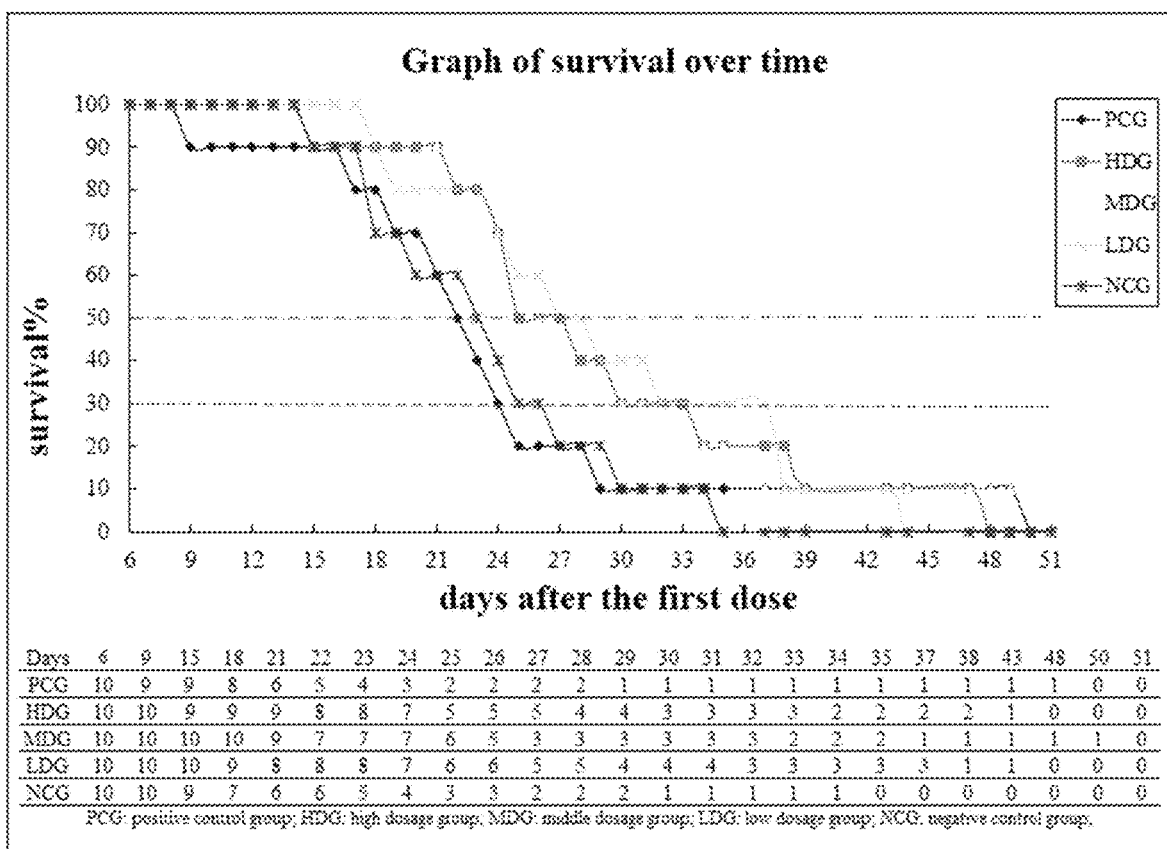

INTRATUMOUR INJECTION FORMULATION

FIELD OF THE INVENTION

The invention is directed to pharmaceutical formulations of anticancer drugs for direct injection into a malignant mass of cancer or sarcoma in a mammal (e.g., human) suffering from malignant disease.

BACKGROUND OF THE INVENTION

Cancer is a group of diseases involving abnormal cell growth with the potential to invade or spread to other parts of the body. Over 100 types of cancers affect humans. The most common types of cancer are: lung (2.09 million cases/year); breast (2.09 million cases/year); colorectal (1.80 million cases/year); prostate (1.28 million cases/year); skin cancer (non-melanoma/year) (1.04 million cases); and stomach (1.03 million cases/year), with the most common cancers in males being lung cancer, prostate cancer, colorectal cancer and stomach cancer and the most common in females being breast cancer, colorectal cancer, lung cancer and cervical cancer. The risk of cancer increases significantly with age, and many cancers occur more commonly in developed countries. Cancer rates also are increasing as more people live to an old age and as lifestyle changes occur in the developing world.

Cancer is a leading cause of death worldwide, accounting for an estimated 9.6 million deaths in 2018. The economic impact of cancer is significant and is increasing. As of 2010, the total annual economic costs of cancer were estimated at 1.16 trillion dollars per year.

Cancer can spread from its original site by local spread, lymphatic spread to regional lymph nodes or by hematogenous spread via the blood to distant sites, known as metastasis. When cancer spreads by a hematogenous route, it usually spreads all over the body. However, as hypothesized in the soil and seed hypothesis of cancer metastasis, cancer 'seeds' grow in certain selected site only ('soil').

The dispersed tumors are called metastatic tumors, while the original tumor is called the primary tumor. Almost all cancers can metastasize and metastasis is common in the late stages of cancer. The typical steps in metastasis are local invasion, intravasation into the blood or lymph, circulation through the body, extravasation into the new tissue, proliferation and angiogenesis. Different types of cancers tend to metastasize to particular organs, but overall the most common places for metastases to occur are the lungs, liver, brain and the bones.

Some of the most common cancer types, such as breast cancer, cervical cancer, oral cancer, and colorectal cancer have high cure rates when detected early and treated according to best practices. While the primary goal is to cure cancer, or to considerably prolong life, improving the patient's quality of life is also an important goal. This can be achieved by supportive or palliative care and psychosocial support.

Cancer is often treated with some combination of radiation therapy, surgery, chemotherapy and/or targeted therapy (heated or cold method), with palliative care particularly important in patients with advanced disease. Most patients suffering from cancer do not die from the cancer at the time of diagnosis or surgery, but rather die from the metastasis and the recurrence of the cancer. For advanced cancer, the chance of survival is small without new formulations and new ways of treatment as therapies beyond radiation, surgery and chemotherapy are often ineffective.

Radiation therapy is only effective for patients who present with clinically localized disease at early and middle stages of cancer, and is not effective for the late stages of cancer with metastasis. Surgery is a traditional approach in which all or part of a tumor is removed from the body but surgery generally is only effective for treating the earlier stages of cancer. More than 50% of cancer patients are no longer candidates for effective surgical treatment by the time they are diagnosed. Further, surgical procedures may increase tumor metastases through blood circulation during surgery.

Chemotherapy, which involves the disruption of cell replication or cell metabolism, works by killing, stopping or slowing the growth of cancer cells, and can be used to shrink tumors that are causing pain and other problems. However, because cancer cells do not greatly differ from normal cells, chemotherapy not only kills fast-growing cancer cells which grow and divide quickly, but also kills or slows the growth of healthy cells that grow and divide quickly. In fact, chemotherapy can kill more healthy cells than cancer cells because there are a greater number of healthy cells in the body. Examples of healthy cells particularly susceptible to chemotherapy because they grow and divide quickly are those that line the mouth and intestines and those that cause hair to grow. Damage to these healthy cells may cause side effects, such as mouth sores, nausea, and hair loss.

Chemotherapy can also cause the following side effects, among others: anemia, appetite loss, bleeding and bruising (thrombocytopenia), constipation, delirium, edema diarrhea, fatigue, fertility issues, hair loss, infection and neutropenia, mouth and throat problems, nausea and vomiting, nerve problems, skin and nail changes, cardial toxicity, lung toxicity, and bone marrow toxicity. Although the side effects often get better or go away after chemotherapy has been completed, for advanced cancer with distal metastasis, adverse effects often cause the patient to be too weak to tolerate further chemotherapy and the severe side effects on the cells of the patient's body—and in particular on the heart, bone marrow and gastrointestinal tract—may result in many advanced stage patients refusing further treatment.

The extreme side effects of anticancer drugs are caused by the poor target specificity of such drugs. The drugs circulate through most normal organs of patients as well as intended target tumors. The poor target specificity that causes side effects also decreases the efficacy of chemotherapy because only a fraction of the drugs is correctly targeted. The efficacy of chemotherapy is further decreased by poor retention of the anti-cancer drugs within the target tumors.

For many years, chemotherapy for malignant disease has been limited to oral, intravenous, intra-artery, intra-peritoneal cavity, and pleural cavity injection.

There are many injectable docetaxel formulations approved for marketing in the U.S., e.g., at a strength of 20 mg/ml, 20 mg/2 ml, 20 mg/0.5 ml, 40 mg/ml, 80 mg/2 ml, 80 mg/4 ml, 80 mg/8 ml, 120 mg/6 ml, 130 mg/13 ml, 140 mg/7 ml, 160 mg/8 ml, 160 mg/16 ml, 200 mg/10 ml and 200 mg/20 ml. In October 2015, Eagle Pharmaceuticals in the U.S. announced a license agreement with Teikoku for the marketing of a new formulation of docetaxel injection. The Eagle docetaxel formulation was described not requiring prior dilution and is available in a 20 mg/ml single-dose vial or in a multiple dose vial of 80 mg/4 ml or 160 mg/8 ml. Each milliliter of the alcohol-free formulation contains 20 mg of docetaxel along with 27.5 mg of soybean oil, 585.0 mg of polysorbate 80, 10.0 mg of citric acid, and 442.2 mg polyethylene glycol 300. For the Eagle formulation, the FDA noted that prior dilution was not necessary and that the medication could be added directly to infusion solution, which could consist of a 250 mL infusion bag or bottle of either 0.9% sodium chloride solution or 5% dextrose solution, with the final concentration between 0.3 mg/mL and 0.74 mg/mL. That product is allegedly covered by two U.S. patents that are listed in the FDA Orange Book—U.S. Pat. Nos. 8,940,786 and 9,308,195. There are other patents and patent filings related to docetaxel formulations, for example, U.S. Patent Publication No. 2008/0319048, which describes lyophilizates of docetaxel wherein a phospholipid and ethanol were used as solvents for lyophilization and U.S. Pat. No. 5,714,512, also part of this patent family and which relates to formulations consisting essentially of docetaxel dissolved in a surfactant selected from polysorbate, polyoxyethylated vegetable oil and polyethoxylated castor oil which are essentially free of ethanol. U.S. Pat. No. 5,698,582 is also part of this patent family and relates to formulations comprising docetaxel dissolved in a surfactant selected from polysorbate or polyethoxylated castor oil which is essentially free of ethanol.

FDA-approved docetaxel injections under 21 U.S.C. § 355(b)(2) (also known as a "505(b)(2) application") fall into two categories. One type consists of two bottles, in which one bottle contains the concentrate of the main drug and the other bottle contains the diluent. The two bottles are pre-mixed uniformly and then glucose or saline is be added for dilution before usage. The other type only consists of one bottle, wherein glucose and saline are directly added to dilute the concentrate of the main drug before usage. This type of product is also called "ready-to-use".

Table 1 below provides an overview of FDA-approved docetaxel injection formulations which have been approved under 505(b)(2):

TABLE 1

| Brand Name | Manufacturer | Approval Date | Dosage | Specification |
|---|---|---|---|---|
| Taxotere ® (Reference) | Sanofi-Aventis | 1996 May 14 | 20 mg/0.5mL 80 mg/2 mL | 2 bottles |
| | | 2010 Aug. 1 | 20 mg/1 mL 80 mg/4 mL 160 mg/8 mL | 1 bottle |
| Docetaxel Injection | Hospira Inc. | 2011 Mar. 8 | 20 mg/2 mL 80 mg/8 mL 160 mg/16 mL | 1 bottle |
| Docetaxel Injection | Accord Healthcare | 2011 Jun. 8 | 20 mg/0.5 mL 80 mg/2 mL | 2 bottles |
| Docetaxel Injection | Sandoz | 2011 Jun. 29 | 20 mg/2 mL 80 mg/8 mL 160 mg/16 mL | 1 bottle |
| Docetaxel Injection (Discontinued) | Apotex Inc. | 2012 Jan. 11 | 20 mg/0.5 mL 80 mg/2 mL | 2 bottles |
| Docetaxel Injection | Actavis LLC | 2013 Apr. 12 | 20 mg/mL 80 mg/4 mL 140 mg/7 mL | 1 bottle |
| Docetaxel Injection (Discontinued) | Pfizer Labs | 2014 Mar. 13 | 20 mg/2 mL 80 mg/8 mL 200 mg/20 mL | 1 bottle |
| Docetaxel Injection | Eagle Pharms | 2015 Dec. 12 | 20 mg/1 mL 80 mg/4 mL 160 mg/8 mL | 1 bottle |

As can be seen from Table 1, the concentration and specifications developed by each company are different, but all of the products need to be diluted to the specified concentration (0.3~0.74 mg/mL) by 5% glucose solution or 0.9% saline before clinical administration.

Table 2 below shows the difference between commercially available docetaxel injection compositions before dilution depending on different manufacture (mg/mL): the compositions contain large amount of polysorbate 80, ethanol or PEG to facilitate the dispersion of docetaxel in water before final intravenous injection.

TABLE 2

| | | Sanofi-Aventis | | | | | | | | |
|---|---|---|---|---|---|---|---|---|---|---|
| | Company | 2 bottles | 1 bottle | Hospira | Accord | Sandoz | Apotex | Pfizer | Actavis | Eagle |
| Composition | Docetaxel | 10 | 20 | 10 | 10 | 10 | 10 | 10 | 20 | 20 |
| | Polysorbate 80 | 260 | 540 | 260 | 260 | 80 | Q.S. | 259 | 424 | 585 |
| | dehydrated ethanol | 88.3 | 395 | Q.S. | 15 | 258.9 | 59.8 | 315.7 | 400 | / |
| | PEG 300 | / | / | Q.S. | / | 648 | 565 | / | / | 442.2 |
| | PEG 400 | / | / | / | 97.5 | / | / | / | / | 0 |
| | Propylene glycol | / | / | / | / | / | 374 | / | / | / |

TABLE 2-continued

| Company | Sanofi-Aventis 2 bottles | 1 bottle | Hospira | Accord | Sandoz | Apotex | Pfizer | Actavis | Eagle |
|---|---|---|---|---|---|---|---|---|---|
| Soybean oil | / | / | / | / | / | / | / | / | 27.5 |
| Polyvinyl Pyrrolidone P12 | / | / | / | / | / | / | / | 100 | / |
| Citric Acid | / | / | 4 | Q.S. | 4 | / | / | 6 | 10 |
| EDTA-2Na | / | / | / | / | / | / | 0.01 | / | / |
| Water | Q.S. | / | / | Q.S. | Q.S. | Q.S. | / | / | / |
| Ready-to-use formulation? | X | ✓ | ✓ | X | ✓ | X | ✓ | ✓ | ✓ |

("Q.S." stands for moderate amount; "/" stands for none)

Paclitaxel is another well-known chemotherapeutic agent that has been approved for use in the U.S. It is available as an injectable formulation in a concentration of 6 mg/ml from a number of pharmaceutical companies. It is also available in a 100 mg vial for use as a suspension for intravenous (IV) infusion. Commercially available formulations of paclitaxel injection contain 50% castor oil and 50% ethanol, with or without polysorbate 80. All of the presently available paclitaxel injection formulations are for intravenous injection only, because castor oil is known to possibly cause an adverse effect (sensitivity) when included in intravenous injections.

Prevention of, or protection from, the side effects of chemotherapy would be a great benefit to cancer patients. Therefore it is a goal of the present invention to provide a deliver system and method capable of administering chemotherapy directly to a malignant mass in a mammal (e.g., human) which does not suffer from the side effects and toxicities of prior art treatments.

OBJECTS AND SUMMARY OF THE INVENTION

It is an object of the present invention to provide formulations and methods for treating a malignant mass in an animal.

It is another object of the present invention to provide a method for administering chemotherapeutic agents to animals (e.g., humans) which reduces the untoward side effects currently experienced with the administration of such agents.

It is another object of the present invention to provide stable formulations of taxanes which are useful in the methods of the present invention.

In accordance with the above objects and others, the present invention is directed to a injectable pharmaceutical formulation of a chemotherapeutic agent(s) dissolved or suspended in a pharmaceutically acceptable carrier for administration directly into a malignant mass in a mammal (e.g., human) In certain preferred embodiments, the injectable pharmaceutical formulation is stable.

The present invention is also directed to a method of treating a malignant mass in a mammal, comprising administering an injectable formulation comprising a therapeutically effective amount of a chemotherapeutic agent dissolved or suspended in a biocompatible carrier directly into the malignant mass. In certain embodiments, the malignant mass may be in a location in the mammal selected from the group consisting of brain, head, eye, mouth, tongue, neck, thyroid, gastrointestinal system, liver, pancreas, gall bladder, lung, respiratory system, urogenital system, breast, lymphatic system, cardiovascular system, nervous system, skin, thorax, pleural membrane, mesothelioma, lung cancer, muscular skeletal system, abdomen with primary or secondary nature. The malignant mass may be one that has metastasized from another organ in the mammal. In certain preferred embodiments, the biocompatible carrier comprises a polyethylene glycol (PEG) or vegetable oil. In certain preferred embodiments, the formulation comprising the chemotherapeutic agent is stable. In certain preferred embodiments, the chemotherapeutic agent comprises an oil-soluble anticancer drug. In certain preferred embodiments, the chemotherapeutic agent is both water insoluble and oil insoluble.

For certain types of cancer, there are limited locations for metastasis. The present invention is particularly useful in such instances, because the tumor and metastasis can be more readily treated by injection and thereby eradicated.

In certain preferred embodiments, the injectable formulation is administered through a syringe or a needle of a fiberscope.

In certain preferred embodiments, the chemotherapeutic agent comprises a taxane. In certain preferred embodiments, the taxane is paclitaxel, or an analogue or prodrug thereof or pharmaceutically acceptable salt thereof. In certain preferred embodiments, the chemotherapeutic agent contains paclitaxel and soybean oil. In certain preferred embodiments, the chemotherapeutic agent contains paclitaxel. In other preferred embodiments, the taxane is docetaxel. In other preferred embodiments, the chemotherapeutic agent comprises a podophyllotoxin derivative such as etoposide or teniposide. In certain preferred embodiments the chemotherapeutic agent comprises camptothecin derivatives, such as hydroxycamptothecin (e.g., 10-hydroxycamptotheicin or 7-ethyl-10-hydroxycamptothecin, including derivatives bonding the phenolic hydroxyl group of 7-ethyl-10-hydroxycamptothecin).

In certain embodiments, the malignant mass is (i) a superficial malignant disease of skin, eye, tongue, mouth, thyroid, breast, cervix, uterus, anus, prostate, vagina, sarcoma of the bone, carcinoma of urethra, etc. and the chemotherapeutic agent can be injected using a syringe directly into the malignant mass, or (ii) a cancer of the nasopharynx and the chemotherapeutic agent can be injected into the malignant mass with the syringe or needle through a nasopharyngoscope; or (iii) a cancer of the liver, kidney and gall bladder and the chemotherapeutic agent can be injected using a syringe through the skin into the malignant mass with the assistance of ultrasound, or via a hole in the abdominal wall made during laparoscopic surgery into the malignant mass; or (iv) a cancer of the ovary, oviduct, pancreas, metastasis of lymph node or direct peritoneum invasion of the abdominal cavity and the chemotherapeutic agent can be injected with the needle into the malignant mass through the holes of a laparoscopic surgery; or (v) a carcinoma or sarcoma of esophagus, stomach, duodenum, small intestine and the chemotherapeutic agent can be injected with the needle into the malignant mass through an enteroscope or through the holes made during laparoscopic surgery or holes made during thoracoscopic surgery; or (vi) a carcinoma or sarcoma of the large intestine and rectum and the chemotherapeutic agent can be injected with the needle into the malignant mass through colonoscopy or through the holes of abdominal wall of laparoscopic surgery; or (vii) a carcinoma or sarcoma of the throat, lung and trachea and the chemotherapeutic agent can be injected with the needle of a fiber bronchoscope into the malignant mass; or (viii) a carcinoma of the lung or of the trachea, the chemotherapeutic agent can be injected with a syringe with the assistance of ultrasound, x-ray, CT scan, MR scan or via the holes of thoracoscopic surgery; or (ix) a carcinoma or sarcoma of the urinary bladder and the chemotherapeutic agent can be injected into the malignant mass with a needle through a cystoscope, or through the holes in the abdominal wall made during laparoscopic surgery;

(x) carcinoma or sarcoma of uterus and the chemotherapeutic agent can be injected into the malignant mass with a syringe of a hysteroscope; or through the holes in the abdominal wall made during laparoscopic surgery;

(xi) a carcinoma or sarcoma of pharynx and larynx and the chemotherapeutic agent can be injected into the malignant mass with a needle through the laryngoscope; or (xii) a carcinoma of the brain and the chemotherapeutic agent can be injected with a needle into the malignant mass after a hole is drilled in the corresponding bone of the skull under the help of X-ray, CT scan or MR scan; or (xii) a carcinoma of the testicle(s), the epididymis, penis, and/or vagina and the chemotherapeutic agent can be injected with a needle into the malignant mass directly without dilution.

The invention is further directed, in part, to injectable formulations for use in the methods of the present invention (direct injection into a malignant mass). In such embodiments, the injectable formulation comprises or consists of one or more chemotherapeutic agents together with a pharmaceutically acceptable excipient(s) which dissolves or suspends the chemotherapeutic agent so that it is able to be directly injected into the malignant mass. Preferably, the injectable formulation is biocompatible and contains only agents that as generally regarded as safe (GRAS).

The invention is further directed in part to an injectable formulation of a taxane, comprising a therapeutically effective amount of a taxane, an analogue or prodrug thereof, or pharmaceutically acceptable salt thereof in a pharmaceutically acceptable carrier for injection comprising or consisting of a PEG having a molecular weight of from about PEG 200 to about PEG 400, and/or to a stable injectable formulation of a taxane, comprising a therapeutically effective amount of a taxane, an analogue or prodrug thereof, or pharmaceutically acceptable salt thereof in a pharmaceutically acceptable carrier for injection consisting of a PEG having a molecular weight from about PEG 200 to about PEG 400, a medium chain triglyceride or a pharmaceutically acceptable vegetable oil. In certain preferred embodiments, the vegetable oil is soybean oil. In certain preferred embodiments, the medium chain triglyceride(s) is selected from the group consisting of caproic acid, caprylic acid, capric acid, lauric acid, and mixtures thereof. In certain preferred embodiments, the taxane is paclitaxel or docetaxel. For paclitaxel, the pharmaceutically acceptable carrier for injection is preferably a medium chain triglyceride.

The present invention is also directed in part to an injectable formulation of a podophyllotoxin derivative, comprising a therapeutically effective amount of the podophyllotoxin derivative in a pharmaceutically acceptable carrier for injection comprising or consisting of a PEG having a molecular weight of from about PEG 200 to about PEG 400, and/or to a stable injectable formulation of a podophyllotoxin derivative, comprising a therapeutically effective amount of a podophyllotoxin derivative, an analogue or prodrug thereof, or pharmaceutically acceptable salt thereof in a pharmaceutically acceptable carrier for injection consisting of a PEG having a molecular weight of from about PEG 200 to about PEG 400, a medium chain triglyceride or a pharmaceutically acceptable vegetable oil. In certain preferred embodiments, the vegetable oil is soybean oil. In certain preferred embodiments, the medium chain triglyceride is medium chain triglycerides is selected from the group consisting of caproic acid, caprylic acid, capric acid, lauric acid, and mixtures thereof. In certain preferred embodiments, the podophyllotoxin derivative is teniposide, etoposide, or a mixture thereof. In certain preferred embodiments, the pharmaceutically acceptable carrier for podophyllotoxin derivatives is a PEG, e.g., a PEG having a molecular weight of from about PEG 200 to about PEG 400.

In certain embodiments, the present invention is directed to an injectable formulation of camptothecin or a derivative(s) thereof, comprising a therapeutically effective amount of hydroxycamptothecin (a camptothecin derivative) in a pharmaceutically acceptable carrier for injection comprising or consisting of a PEG, e.g., a PEG having a molecular weight of from about PEG 200 to about PEG 400; or a stable injectable formulation of a camptothecin derivative, comprising a therapeutically effective amount of a hydroxycamptothecin, an analogue or prodrug thereof, or pharmaceutically acceptable salt thereof in a pharmaceutically acceptable carrier for injection consisting of a PEG, e.g., a PEG having a molecular weight from about PEG 200 to about PEG 400, a medium chain triglyceride or a pharmaceutically acceptable vegetable oil, and most preferably a PEG.

The invention is further directed to a kit, comprising a first vial containing a crystallized, powdered, or lyophilized chemotherapeutic agent, and a second vial containing the pharmaceutically acceptable excipients needed to deliver the chemotherapeutic agent to a tumor, the pharmaceutically acceptable excipients including a PEG having a molecular weight from about PEG 200 to about PEG 400, a medium chain triglyceride, ethanol, or a pharmaceutically acceptable vegetable oil.

In certain embodiments, the chemotherapeutic agent is insoluble in water. In certain embodiments, the chemotherapeutic agent is a taxane (e.g., paclitaxel, docetaxel), hydroxycamptothecine, teniposide, etososide, D Dantinomycin, carmustine, etc. and the injectable composition preferably contains one or more organic excipients as non-aqueous solvents, including but not limited to, soybean oil, castor oil, sesame oil, peanut oil, medium-chain triglycerides, coconut oil, fish oil, cottonseed oil, corn oil, olive oil, peach kernel oil, or any other pharmaceutically acceptable oil for injection that can dissolve or suspend the chemotherapeutic agent sufficiently to inject it into desired site, e.g., a malignant mass. In certain embodiments, the injectable composition does not contain other solvents. In other embodiments the injectable formulation contains alcohol. In other embodiments, the injectable formulation does not contain any alcohol. In other embodiments, the injectable composition further contains one or more pharmaceutically acceptable excipients, such as, but not limited to, ethyl oleate, benzyl benzoate, polysorbate, PEG, cholesterol, phospholipid, propylene glycol, glycerin, ethyl alcohol, niacinamide, dimethyl sulfoxide, nutmeg isopropanol, dimethylacetamide, surfactants (e.g., non-ionic surfactants), etc. In certain preferred embodiments, the injectable composition is for direct injection into local cancer tissue, and is not intended for venous injection. In certain embodiments, the injectable composition includes two or more chemotherapeutic agents.

Medium chain triglycerides are triglycerides whose fatty acids have an aliphatic tail of 6-12 carbon atoms. Examples of medium chain triglycerides which are useful as solvents in the present invention include caproic acid, caprylic acid, capric acid, lauric acid, and mixtures thereof.

In certain embodiments of the present invention, there is provided an injectable formulation of a taxane, comprising a therapeutically effective amount of a taxane, an analogue thereof, or pharmaceutically acceptable salt thereof in a pharmaceutically acceptable carrier for injection comprising or consisting of from about 70% to about 100% of a pharmaceutically acceptable hydroalcoholic solvent (e.g., ethanol). In certain preferred embodiments, the taxane is paclitaxel. In other preferred embodiments, the taxane is docetaxel.

In order for the invention described herein to be more fully understood, the following definitions are provided for the purposes of this disclosure:

The term "patient" broadly refers to any animal that is to be treated with the compositions and by the methods herein disclosed. The present formulations and methods can provide treatment to any animal, e.g., any vertebrate, including but not limited to human (preferred embodiments), primates, dogs, cats, horses, cattle, etc. In preferred embodiments, the patient is human. The patient (such as human) may have advanced disease or lesser extent of disease, such as low tumor burden. In some embodiments, the patient is at an early stage of a proliferative disease (such as cancer). In other embodiments, the patient is at an advanced stage of a proliferative disease (such as an advanced cancer).

As used herein, the term "unit dose" refers to physically discrete units suitable as unitary dosages for mammalian subjects.

The term "comprising" is an inclusive term interpreted to mean containing, embracing, covering or including the elements listed following the term, but not excluding other unrecited elements.

A "therapeutically effective amount" means the amount that, when administered to an animal for treating a disease, is sufficient to produce a desired therapeutic effect (e.g. to affect treatment for that disease).

As used herein, the term "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The terms "composition" and "formulation" are used interchangeably herein.

The term "stable" as applied to the formulations of the present invention means for the purposes of the present invention that the formulation has acceptable levels of impurities when stored at temperatures between 5° C. and 20° C., and preferably between 5° C. and 40° C., for a period of at least 14 days. An acceptable level of impurities is considered for the purposes of the present invention a total level of impurities of equal to or less than 2% of the total amount of the drug contained in the formulation. In other embodiments where the drug is a taxane such as paclitaxel, stability can also be defined as containing amounts of commonly found individual impurities for such taxanes. For example, for paclitaxel, stability can be defined as a formulation containing equal to or less than 0.8% of baccatin, equal to or less than 0.4% of ethyl ester side chain, equal to or less than 0.8% of 10-deacetyl paclitaxel, equal to or less than 0.6% of 7-epi-10-deacetyl-paclitaxel, equal to or less than 0.6% of 7-epi-10 paclitaxel, and/or equal to or less than 0.1% of other largest impurity. Thus, stability in certain embodiments is based on total impurities; and in other embodiments is based on one or more of the impurities mentioned in the last sentence.

BRIEF DESCRIPTION OF THE DRAWINGS

The FIGURE provides the survival of different mice groups over time, after the first injection of chemotherapy in Example 16 (paclitaxel oil).

DETAILED DESCRIPTION OF THE INVENTION

The invention will be described with reference to various specific and preferred embodiments and techniques, however, it should be understood that many variations and modifications can be made while remaining with the spirit and scope of the invention.

In current practice, the standard treatment of most potentially curable solid tumors is surgical removal often followed by chemotherapy. For the major cancer killers such as lung, breast, and colorectal cancer, the administration of chemotherapy after the tumor is surgically removed may eradicate micrometastatic disease (disease undetectable using conventional imaging technologies) in those patients who still harbor residual cancer cells after surgery. However, this treatment is often unsuccessful, and the chemotherapy is often limited by the side effects caused by such agents (as previously explained above).

Chemotherapeutic Agents

In preferred embodiments of the invention, therapeutically effective amounts of one or more pharmaceutically acceptable chemotherapeutic agents are incorporated into the injectable formulations of the invention.

Any chemotherapeutic (e.g., anticancer) agent (drug) can be used to inject directly into the malignant mass of the animal (e.g., human). Preferably, the chemotherapeutic agent is soluble in oil because the membrane of the cancer cell has a double lipid layer structure. Thus, if the drug is lipid soluble, it can enter the cancer cell easily. A chemotherapeutic agent injected into a vein or an artery of the cancer can be carried away from the tumor without entering into the cancer cell, and therefore the efficacy (e.g., cell-killing effect) is weak. In contrast, when the lipid-dissolved chemotherapeutic agent is directly injected into the tumor, it can exert its effect over a longer duration and can enter the cancer cell more easily.

Examples of chemotherapeutic agents useful in the formulations of the invention include taxanes, or analogues or prodrugs thereof, and salts thereof. Taxanes are diterpene chemotherapeutic agents which function in part by disrupting microtubule function, resulting in inhibition of cell division.

Preferably, the taxane is selected from the group consisting of paclitaxel, docetaxel, cabazitaxel, taxadiene, baccatin III, taxchinin A, brevifoliol, and taxuspine D, or a pharmaceutically acceptable salt thereof. In certain embodiments, the taxane is selected from the group consisting of paclitaxel, docetaxel, and cabazitaxel, or a pharmaceutically acceptable salt thereof. In certain preferred embodiments, the taxane is paclitaxel, an analogue or prodrug thereof, and/or pharmaceutically acceptable salts thereof.

An "analog" of paclitaxel as used herein refers to a compound generated by replacing one or more atoms or functional groups of paclitaxel. The most well-known paclitaxel analog is the semi-synthetic analog docetaxel (Taxotere®), which has been approved for treatment of a wide range of cancers, including lung cancer, breast cancer, and prostate cancer. Other paclitaxel derivatives include, but are not limited to, cabazitaxel (Jevtana®), which is approved for treatment of prostate cancer, DJ-927 (Tesetaxel®), XRP9881 (Larotaxel®), BMS-275183, ortataxel, and RPR 109881A, and BMS-184476. A "prodrug" of paclitaxel as used herein refers to a compound that it is converted to paclitaxel following administration to a subject. Examples of paclitaxel prodrugs include, but are not limited to, DHA-paclitaxel (Taxoprexin®) and paclitaxel polyglumex (Opaxio®), both of which are in clinical development.

As used herein, "pharmaceutically acceptable salts" of the taxanes are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the taxanes. The term "salts" refers to the relatively non-toxic, inorganic and organic acid addition salts of taxanes. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like.

Paclitaxel has been shown to have significant antineoplastic and anticancer effects in drug-refractory ovarian cancer and has shown excellent antitumor activity in a wide variety of tumor models, as well as inhibiting angiogenesis when used at very low doses (Grant et al., Int. J. Cancer, 2003).

The poor aqueous solubility of paclitaxel, however, presents a problem for human administration, because when oral delivery is not effective, the delivery of drugs that are inherently insoluble or poorly soluble in an aqueous medium can be seriously impaired. Accordingly, currently used paclitaxel formulations (e.g., Taxol®) require a Cremophor® and/or ethanol to solubilize the drug.

Administration of Formulation

The chemotherapeutic agent(s) used in the injectable formulations and treatments of the present invention are preferably dosed in therapeutically effective amounts known to those skilled in the art. In certain embodiments, the therapeutically effective amount is an amount that yields a maximum therapeutic effect. In other embodiments, the therapeutically effective amount yields a therapeutic effect that is less than the maximum therapeutic effect. For example, a therapeutically effective amount may be an amount that produces a therapeutic effect while avoiding one or more side effects associated with a dosage that yields maximum therapeutic effect. One skilled in the clinical and pharmacological arts will be able to determine a therapeutically effective amount through routine experimentation, namely by monitoring a subject's response to administration of the agent and adjusting the dosage accordingly. For additional guidance, see, e.g., Remington: The Science and Practice of Pharmacy, $22^{nd}$ Edition, Pharmaceutical Press, London, 2012, and Goodman & Gilman's The Pharmacological Basis of Therapeutics, $12^{th}$ Edition, McGraw-Hill, New York, N.Y., 2011, the entire disclosures of which are incorporated by reference herein.

Paclitaxel (Abraxane®) is approved for the treatment of metastatic breast cancer (recommended dose is 260 mg/m$^2$ intravenously over 30 minutes every 3 weeks. For non-small cell lung cancer, the recommended dosage is 100 mg/m$^2$ over 30 minutes on days 1, 8 and 15 of each 21-day cycle. For adenocarcinoma of the pancreas, the recommended dosage of abraxane is 125 mg/m$^2$ intravenously over 30-40 minutes on days 1, 8 and 15 of each 28-day cycle). It is supplied as sterile lyophilized powder for reconstitution before use (using 0.9% sodium chloride injection for reconstitution). That formulation comprises albumin-bound nanoparticles for injectable suspension with a mean particle size of about 130 nm. The dose of the paclitaxel administration via direct injection is in accordance with the present invention. and therefore may be reduced as compared to a commonly used intravenous dose. On the other hand, it is also possible that the paclitaxel dose may be increased, as other tissues in the body will not be exposed to the drug to the same extent as intravenous administration, resulting in decreased side effects.

Examples of suitable dosages of paclitaxel in accordance with the present invention are set forth in Table 3 below. The amount of the injection liquid used is according to the size or volume of the tumor.

TABLE 3

| Paclitaxel Injection (5 ml: 30 mg) USAGE AND DOSAGE ||||||| 
|---|---|---|---|---|---|---|
| tumor length (cm) | tumor width (cm) | tumor height (cm) | gross tumor volume (cm$^3$) | Local administration volume (ml) | Local administration content (mg) | Local administration frequency |
| 1 | 1 | 1 | 0.5 | 0.03 | 0.2 | once every 1-2 weeks |
| 2 | 2 | 2 | 4.2 | 0.21 | 1.3 | |
| 3 | 3 | 3 | 14.1 | 0.71 | 4.3 | |
| 4 | 4 | 4 | 33.5 | 1.7 | 10.0 | |
| 5 | 5 | 5 | 65.4 | 3.3 | 19.8 | |

TABLE 3-continued

Paclitaxel Injection (5 ml: 30 mg) USAGE AND DOSAGE

| tumor length (cm) | tumor width (cm) | tumor height (cm) | gross tumor volume (cm³) | Local administration volume (ml) | Local administration content (mg) | Local administration frequency |
|---|---|---|---|---|---|---|
| 6 | 6 | 6 | 113.0 | 5.7 | 34.2 | |
| 7 | 7 | 7 | 179.5 | 9.0 | 54 | |
| 8 | 8 | 8 | 267.9 | 13.4 | 80.4 | |
| 9 | 9 | 9 | 381.5 | 19.1 | 114.6 | |
| 10 | 10 | 10 | 523.3 | 26.2 | 157.0 | |

1. gross tumor volume (cm³): V1 = π/6 × a × b × c
2. Local administration volume (ml): V2(ml) = V1 × 5%
3. Local administration content (mg) = V2 (mL) * 6

As noted above, potential applications of the formulations of the invention include direct administration (e.g., injection) into a malignant cancer or sarcoma mass in the body. In certain embodiments, potential treatment sites include, but are not limited to, the following cancers or tumors: a hepatocellular carcinoma, a metastatic cancer of the liver, an advanced hepatocellular carcinoma, a pancreatic cancer, an adenocarcinoma, a mastocytoma or a mast cell tumor, an ovarian cancer, a non-small cell lung cancer, a small cell lung cancer, melanoma, retinoblastoma, breast tumor, colorectal carcinoma, a histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer, breast cancer, genitourinary cancer, lung cancer, gastrointestinal cancer, epidermoid cancer, melanoma. In a broader sense of the invention, the formulations and treatments of the invention may be used to treat a proliferative disease selected from hyperproliferative conditions such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. In certain embodiments, the formulations and treatments are used with respect to gastrointestinal cancers other than pancreatic cancer. In some embodiments, the proliferative disease is cancer. In some embodiments, the proliferative disease is a non-cancerous disease. In some embodiments, the proliferative disease is a benign or malignant tumor, and encompasses metastasis in the original organ or tissue and/or in any other location of the tumor. In some embodiments, there is provided a method of treating a primary tumor. In some embodiments, there is provided a method of treating cancer that has metastasized from the primary tumor. In some embodiments, there is provided a method of treating cancer at advanced stage(s). In some embodiments, there is provided a method of treating breast cancer (HER2 positive or HER2 negative), including, for example, advanced breast cancer, stage IV breast cancer, locally advanced breast cancer, and metastatic breast cancer. In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies, melanoma (including metastatic melanoma), colorectal cancer, pancreatic cancer, and solid tumors (such as advanced solid tumors).

In the methods of the invention, the chemotherapeutic agent is preferably administered directly into the malignant mass of the cancer or sarcoma of the body via (direct) injection. For superficial malignant disease of skin, eye, tongue, mouth, thyroid, breast, cervix, uterus, anus, prostate, vagina, sarcoma of the bone, carcinoma of urethra, etc., the chemotherapeutic agent can be injected with the syringe directly into the malignant mass without dilution.

In certain embodiments of the invention, the injectable formulation of the invention is injected with a syringe directly into a malignant mass. This embodiment is particularly useful, e.g., for cancer of the liver, kidney, gall bladder, ovary, oviduct, pancreas, metastasis of lymph node or direct peritoneum invasion of the abdominal cavity.

In additional embodiments, the invention is particularly useful, e.g., for superficial malignant diseases of the skin, eye, tongue, mouth, thyroid, breast, cervix, uterus, anus, prostate, vagina, sarcoma of the bone, carcinoma of urethra, etc.

In certain embodiments of the invention, the injectable formulation of the invention is injected into the malignant mass with a syringe or needle through a nasopharyngoscope. This embodiment is particularly useful, e.g., for a cancer of the nasopharynx.

In certain embodiments of the invention, the injectable formulation of the invention is injected using a syringe through the skin into the malignant mass with the assistance of ultrasound, or via a laparoscope into the malignant mass. This embodiment is particularly useful, e.g., for cancer of the liver, kidney and gall bladder.

In certain embodiments of the invention, the injectable formulation of the invention is injected laparoscopically with a needle into the malignant mass. This embodiment is particularly useful, e.g., for cancer of the ovary, oviduct, pancreas, metastasis of lymph node or direct peritoneum invasion of the abdominal cavity.

In certain embodiments of the invention, the injectable formulation of the invention is injected into a malignant mass through an enteroscope or via combination therapy with a laparoscopic or thoracoscopic surgery. This embodiment is particularly useful, e.g., for a carcinoma or sarcoma of esophagus, stomach, duodenum, and/or small intestine.

In certain embodiments of the invention, the injectable formulation of the invention is injected with the needle into the malignant mass through colonoscopy or combination therapy with the laparoscopic surgery. This embodiment is particularly useful to treat, e.g., a carcinoma or sarcoma of large intestine and/or rectum.

In certain embodiments of the invention, the injectable formulation of the invention is injected with the needle of a fiber bronchoscope into the malignant mass. This embodiment is particularly useful to treat, e.g., a carcinoma or sarcoma of the throat, lung and/or trachea.

In certain embodiments of the invention, the injectable formulation of the invention is injected with the syringe under the help of ultrasound, x-ray, CT scan, MR scan or via the hole of a thoracic wall of thoracoscopic surgery. This embodiment is particularly useful to treat, e.g., a carcinoma of the lung and thorax, lymphoma of the thorax or lymph node metastasis in the thorax.

In certain embodiments of the invention, the injectable formulation of the invention is injected into the malignant mass with a needle through a cystoscope, or through the hole made in the abdominal wall during laparoscopic surgery. This embodiment is particularly useful to treat, e.g., a carcinoma or sarcoma of the urinary bladder.

In certain embodiments of the invention, the injectable formulation of the invention is injected into the malignant mass with a syringe or a needle via a hysteroscope. This embodiment is particularly useful to treat, e.g., a carcinoma or sarcoma of the uterus, a carcinoma of the cervix, a carcinoma of the endothelium of the uterus.

In certain embodiments of the invention, the injectable formulation of the invention is injected into the malignant mass with a needle through a laryngoscope. This embodiment is particularly useful to treat, e.g., a carcinoma or sarcoma of pharynx and/or larynx.

In certain embodiments of the invention, the injectable formulation of the invention is injected with the needle into the malignant mass after a hole is drilled in the corresponding bone of the skull under the help of X-ray, CT scan or MR scan. This embodiment is particularly useful to treat, e.g., a carcinoma of the brain.

One skilled in the art will appreciate that the doses for the cancer or sarcoma of different organs is dependent on the size or volume of the mass to be treated.

In certain preferred embodiments, the formulation comprises or consists of a therapeutically effective dose (e.g., about 60 mg) paclitaxel in 5 ml of pharmaceutically acceptable carrier (e.g., PEG300). In certain preferred embodiments, the concentration of paclitaxel is about 30 mg of paclitaxel in 5 ml of pharmaceutically acceptable carrier (e.g., PEG 300). In such formulations the concentration of paclitaxel as an injectable formulation is 6 mg/ml. In general, the dosage is about 1 to 10 ml of the solution or suspension that depend on the size or volume of the mass. The volume of the drug used preferably should be smaller than 8% of the mass; otherwise the liquid will flow out of the injection site.

In certain embodiments, the injectable formulation of the invention is administered more than once. For example, in certain embodiments, the injectable formulation is administered once per week, per month, or once every two months. The number of injections and the time between injections is within the knowledge of those skilled in the art, and is dependent in part on the size of the tumor.

In certain embodiments, the injectable formulation is administered using a fiberscope, particularly in places that are hard to reach via injection. The use of a fiberscope is considered minimally invasive surgery. It is contemplated that the chemotherapeutic agent can be administered to a tumor within the intracerebral, intrathoracic or intraperitoneal cavity through the use of a fiberscope, laparoscope, thoracoscope or other medical instrument. For example, in certain embodiments wherein the primary tumor has metastasized, the injectable formulations of the present invention are administered to both the primary malignant mass and any secondary tumors. By virtue of the present invention, it is much easier to treat multiple sites, because in the past a surgeon had great difficulty to operate in more than two organs of a patient at the same time, e.g., in the abdomen, lung and brain at the same time due to the trauma to the cancer patient.

The methods of the present invention allow for both less trauma to the patient and the killing of cancer cells but not normal cells (which occurs when the chemotherapeutic agent is systemically administered). The direct injection of the chemotherapeutic agent into the malignancy also greatly reduces or eliminates many common side effects. For example, replacing surgery with direct injection of the chemotherapeutic agent into the malignancy prevents disfigurement of the face of a patient with carcinoma of tongue or mouth, the loss of breast in a patient with breast cancer, amputation of a leg in a patient with sarcoma, loss of the uterus of a patient with cancer of cervix or early stage cancer of the uterus. Direct injection of the chemotherapeutic agent in to the malignancy also reduces or eliminates side effects such as myelosuppression, neurotoxicity, lung injury, pulmonary fibrosis, acute cardiotoxicity, left ventricular dysfunction, heart failure, intracardiac conduction disorders and arrhythmias, pericarditis, muscle and/or joint pain, gastrointestinal reactions, and/or alopecia.

Cancer 'seeds' grow in certain selected sites only ('soil') as hypothesized in the soil and seed hypothesis of cancer metastasis. If the metastasis and the primary mass of malignant is small, it cannot threaten the life of patient. If the tumor is large, it can be detected easily with the help of the CT scan or MR scan or fiberscope. With the assistance of a fiberscope and/or laparoscope, formulations of the invention (containing a chemotherapeutic or anti-cancer drug) can be injected directly into a large tumor without affecting the normal (surrounding) tissue, enabling the killing of cancer cells, enabling the stopping or delaying the growth of the malignant mass (e.g., making the mass smaller or shrinking the tumor), and enabling patients with advanced cancer to live with the tumor (in similar fashion to human patients living with a parasite). When the chemotherapeutic or anti-cancer drug is injected into the tumor, the drug will flow along the blood vessel or the lymphatic vessel to the metastasis, and it will kill the metastasis cell. The injection of chemotherapeutic agent into the tumor results in little trauma to the patient and can be repeated, e.g., many times per month. The direct injection also can be administered at the same time to both the primary tumor and a secondary tumor to which the cancer has metastasized.

Combination Therapy

In certain embodiments of the present invention, the chemotherapeutic agent (e.g., paclitaxel) is administered in combination with additional (one or more) agents to treat the cancer or sarcoma. For example, in certain embodiments the chemotherapeutic agent is a taxane (e.g., paclitaxel) and is administered along with one or more antibodies, such as an alemtuzumab, a brentuximab vedotin, a cetuximab, a gemtuzumab, ozogamicin, an abritumomab tiuxetan, a nimotuzumab, an ofatumumab, a panitumumab, a rituximab, a tositumomab, or a trastuzumab, or an antagonistic FGFR3 antibody as described in U.S. Patent Publication No. 2018/0222983, hereby incorporated by reference in its entirety. In other embodiments, the treatment may further include treatment with other antibodies such as, e.g., antibodies against one or more of IL-6, HGF, PGE-2, PGF, TGF-beta, PDGF-BB, MCP-1 and MMP-9 or their receptors. In another embodiment, the compound or composition is or includes a neu-1 sialidase inhibitor such as oseltamivir phosphate that can prevent receptor dimerization triggered by these ligand-receptor interactions and hence prevent downstream activation. In other embodiments, the compound or composition is or includes a small molecule inhibitor of the transcriptional activators triggered by these distinct ligand-receptor interactions, including inhibitors of transcriptional activators such as NF-kb and Stat-3, among others. Other therapeutic agents that may be employed to disrupt the effects of these distinct ligand receptor interactions are miRNA therapeutics that disrupt the post-transcriptional activity of target genes upregulated by the distinct ligand-receptor interactions described above.

Other therapeutic agents which may be used in combination with the formulations and methods of the invention include, but are not limited to, a water soluble or insoluble anticancer drug, a doxorubicin or a carboplatin, an inducer of apoptosis or a mitotic inhibitor or anti-microtubule inhibitor, an alkylating agent, a nucleoside or nucleotide analog, a topoisomerase inhibitor. Optionally, the inducer of apoptosis or a mitotic inhibitor or anti-microtubule inhibitor comprises or consists of a raltitrexed or equivalent, or Tomudex®; a doxorubicin or equivalent, or Adriamycin®; a fluorouracil or 5-fluorouracil or equivalent; an epothilone or an epothilone A, B, C, D, E or F or equivalent; an ixabepilone (also known as azaepothilone B) or equivalent, or BMS-247550™; a vincristine (also known as leurocristine) or equivalent, or Oncovin®; a vinblastin, vinblastine, vindesine, vinflunine, vinorelbine or Navelbine® or equivalent; or, any combination thereof, and optionally the alkylating agent comprises or consists of a temozolomide, (TMZ) (Temodar®, Temodal® or Temcad®), a cisplatin or equivalent; a cisplatinum or equivalent; a cis-diamminedichlorideplatinum(II) (CDDP) or equivalent; a carboplatin or equivalent; a oxaloplatin or equivalent; a cyclophosphamide (cytophosphane) or equivalent, or Endoxan®, Cytoxan®, Neosar®; a mechlorethamine or equivalent; a chlormethine or equivalent; a mustine or equivalent; a nitrogen mustard or equivalent; a chlorambucil or equivalent, or Leukeran®; or a combination thereof, and optionally the topoisomerase inhibitor comprises or consists of an etoposide or equivalent, or Eposin®, Etopophos®, Vepesid® or VP-16®; an amsacrine or equivalent; a topotecan or equivalent, or Hycamtin®; a teniposide or equivalent, or Vumon® or VM-26®; an epipodophyllotoxin or equivalent; a camptothecin or equivalent; an irinotecan or equivalent, or Camptosar®; or combinations of any of the foregoing.

In some embodiments, the additional chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), Navelbine® (vinorelbine), anthracycline (Doxil®), methyl-CCNU, cisplatin, etoposide, interferons, camptothecin and derivatives thereof, phenesterine, topetecan, vinblastine, vincristine, tamoxifen, piposulfan, nab-5404, nab-5800, nab-5801, Irinotecan, HKP, Ortataxel®, gemcitabine (Gemzar®), Herceptin®, vinorelbine, capecitabine (Xeloda®), pemetrexed (Alimta®), bevacizumab (Avastin®), bortezomib (Velcade®), erlotinib (Tarceva®), pegfilgrastim (Neulasta®), Lapatinib (GW57016), Sorafenib, derivatives thereof, chemotherapeutic agents known in the art, and the like.

In some embodiments, the chemotherapeutic agent is an antagonist of other factors that are involved in tumor growth, such as EGFR, ErbB2 (also known as Herb), ErbB3, ErbB4, or TNF. Sometimes, it may be beneficial to also administer one or more cytokines to the patient. In some embodiments, the therapeutic agent is a growth inhibitory agent. Suitable dosages for the growth inhibitory agent are those presently used and may be lowered due to the combined action (synergy) of the growth inhibitory agent and the taxane.

In some embodiments, the chemotherapeutic agent is a chemotherapeutic agent other than an anti-VEGF antibody, a HER2 antibody, interferon, and an HGfB antagonist.

Manufacture

The injectable formulation of the invention may be prepared for use in any of a variety of ways known to those skilled in the art. The formulation may be prepared in advance and stored until needed, in sterile form with the optional inclusion of effective amounts of preservatives. Alternatively, it may be preferable to store the active ingredient(s) of the injectable formulation (chemotherapeutic agent, e.g., anticancer drug) in solid form and reconstitute the formulation into an injectable formulation at a time shortly before it is to be administered, i.e., one hour or less prior to use, or preferably about fifteen minutes prior to use. In such a case, the chemotherapeutic agent is stored separately from the aqueous liquid.

Prior to use, the chemotherapeutic agent (e.g., a taxane) is preferably contained in a pharmaceutical acceptable carrier. Examples of pharmaceutically acceptable carriers include one or more of PEG, vegetable oil, medium chain triglycerides, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers must be compatible with both the components of the composition and the (e.g., human) patient. Other examples of non-aqueous solvents include propylene glycol and other glycols, metabolizable oils, aqueous carriers including water and alcoholic/aqueous solutions, and emulsions or suspensions (eg. saline and buffered media).

In certain preferred embodiments, the formulation of the invention comprises or consists of the chemotherapeutic agent(s) together with an oil, a medium chain triglyceride, or a PEG. In certain preferred embodiments the PEG has a molecular weight from about 100 to about 600, preferably from about 200 to about 400 or preferably from about 200 to about 300 and most preferably the PEG is selected from PEG 200, PEG 300, PEG 400, and mixtures of any of the foregoing. In certain preferred embodiments, the chemotherapeutic agent is a taxane (e.g., paclitaxel).

In certain embodiments, the chemotherapeutic agent is insoluble in water. In certain embodiments, the chemotherapeutic agent is a taxane (e.g., paclitaxel, docetaxel), hydroxycamptothecine, teniposide, etososide, D Dantinomycin, carmustine, etc. In such embodiments, the injectable composition preferable contains one or more organic excipients as non-aqueous solvents, including but not limited to soybean oil, castor oil, sesame oil, peanut oil, medium-chain triglycerides, coconut oil, fish oil, cottonseed oil, corn oil, olive oil, peach kernel oil, or any other pharmaceutically acceptable oil for injection that can dissolve or suspend the chemotherapeutic agent sufficiently to inject it into desired site, e.g., the malignant mass. In certain embodiments, the injectable composition does not contain other solvents. In other embodiments the injectable formulation contains alcohol. In other embodiments, the injectable formulation does not contain any alcohol. In other embodiments, the injectable composition further contains one or more pharmaceutically acceptable excipients, such as but not limited to ethyl oleate, benzyl benzoate, polysorbate, PEG, cholesterol, phospholipid, propylene glycol, glycerin, ethyl alcohol, niacinamide, dimethyl sulfoxide, nutmeg isopropanol, dimethylacetamide, surfactants (e.g., non-ionic surfactants), etc. In certain preferred embodiments, the injectable composition is for direct injection into local cancer tissue, and is not intended for venous injection. In certain embodiments, the injectable composition includes two or more chemotherapeutic agents.

If the taxane (e.g., paclitaxel) is dissolved with castor oil (similarly to the marketed product by Eagle Pharmaceuticals discussed infra), or with polysorbate 80, it is difficult to withdraw by a small needle of the syringe or fiberscope. On the other hand, if it is diluted with ethanol the concentration of the drug is unstable and produces too high a level of impurities.

In certain preferred embodiments, the solvent used to dissolve the taxane (e.g., paclitaxel or docetaxel) has a viscosity in the range from, e.g., about 1 $mm^2/s$ to about 2000 $mm^2/s$. Examples of the viscosities of certain solvents useful in the present invention are set forth in Table 4 below:

TABLE 4

| No. | Name | Temp. (° C.) | Kinematic viscosity measurement ($mm^2/s$) |
|---|---|---|---|
| 1 | Dehydrated ethanol | 25 | 1.41 |
| 2 | Medium Chain Triglyceride | 25 | 23.85 |
| 3 | Soybean Oil | 25 | 50.72 |
| 4 | PEG-300 | 25 | 71.54 |
| 5 | PEG-400 | 25 | 89.30 |
| 6 | Polysorbate 80 | 25 | 503.7 |
| 7 | Polyoxyl(35) Caster Oil | 25 | 642.9 |
| 8 | Glycerol | 25 | 908.8 |

Table 5 below provides the solubility of certain preferred chemotherapeutic agents in biocompatible pharmaceutical solvents which may be used in the injectable formulations of the present invention.

TABLE 5

| Raw Material | Solubility of Antineoplastic drugs (25° C.) | | TEMP.VARIATION |
|---|---|---|---|
| | Solvent | Solubility | API Soluble |
| Docetaxel | Medium Chain Triglycerides | <10 mg/mL | 30 mg/mL-35 mg/mL at 105° C. |
| | soybean oil | <10 mg/mL | 12.5 mg/mL-15 mg/mL at 140° C. |
| | dehydrated ethanol | 118.4 mg/mL-126.38 mg/mL | |
| | Tween®-80 | <40 mg/mL | >40 mg/mL at 120° C. |
| | PEG-400 | <10 mg/mL | >40 mg/mL at 110° C. |
| | N-N dimethylacetylamide | >50 mg/mL | |
| | glycerin | <1 mg/mL | |
| Paclitaxel | Medium Chain Triglycerides | <6 mg/mL | >6 mg/mL at 120° C. |
| | soybean oil | <6 mg/mL | >6 mg/mL at 145° C. |
| | Dehydrated ethanol | >6 mg/mL | |
| | Tween®-80 | <6 mg/mL | >6 mg/mL at 110° C. |
| | PEG-400 | <40 mg/mL | >40 mg/mL at 110° C. |
| | N-N dimethylacetylamide | >50 mg/mL | |
| | glycerin | <1 mg/mL | |
| Teniposide | Medium Chain Triglycerides | <0.2 mg/mL | <0.2 mg/mL at 200° C. |
| | Dehydrated ethanol | <0.13 mg/mL | |
| | Tween®-80 | <1.7 mg/mL | |
| | N-N dimethylacetylamide | >105.3 mg/mL | |
| | PEG-300 | <10 mg/mL | >50 mg/mL at 140° C. |
| | glycerin | <1 mg/mL | |
| Hydroxycamptothecine | Medium Chain Triglycerides | <1 mg/mL | |
| | dehydrated ethanol | <1 mg/mL | |
| | Tween®-80 | <1 mg/mL | |
| | N-N dimethylacetylamide | About 71.43 mg/mL | |
| | PEG-300 | <10 mg/mL | >10 mg/mL at 90° C. |
| | glycerin | <1 mg/mL | |

In certain embodiments, a combination of solvents may be used in order to prepare the injection formulations of the present invention. Suitable combinations are provided, e.g., in Table 6 below:

TABLE 6

Mutual solubility form of solvent in pairs

| | | |
|---|---|---|
| alcohol anhydrous | N,N-dimethylacetamide | mutually soluble |
| | soybean oil | non-mutually soluble |
| | Medium Chain Triglycerides | non-mutually soluble |
| | PEG400 | mutually soluble |
| | Tween ®-80 | mutually soluble |
| N,N-dimethylacetamide | soybean oil | mutually soluble |
| | Medium Chain Triglycerides | mutually soluble |
| | PEG400 | mutually soluble |
| | Tween ®-80 | mutually soluble |
| soybean oil | Medium Chain Triglycerides | mutually soluble |
| | PEG400 | non-mutually soluble |
| | Tween ®-80 | mutually soluble |
| Medium Chain Triglycerides | PEG400 | non-mutually soluble |
| | Tween ®-80 | non-mutually soluble |
| polyethylene glycol (PEG400) | Tween ®-80 | mutually soluble |
| glycerine | Dehydrated ethanol | mutually soluble |
| | N,N-dimethylacetamide | mutually soluble |
| | soybean oil | mutually soluble |

Formation or reconstitution of the formulation (liquid or suspension) is achieved by any conventional mixing method, either manually or by the use of mixing equipment. The particulate material may be stored in a sterile environment, as a unit dose, and the container may include instructions concerning the amount of liquid carrier (e.g., sterile water such as water for injection) to be added to achieve the prior viscosity of the formulation.

In certain embodiments, the formulation includes a pharmaceutically acceptable surfactant. Suitable surfactants include polysorbates such as, but not limited to, polysorbate 80 (Tween® 80) and any combinations or mixtures thereof. In certain other embodiments, the base may be a combination of a pharmaceutically acceptable surfactant and solvent. Other bases may include, sodium stearyl fumarate, diethanolamine cetyl sulfate, isostearate, polyethoxylated castor oil, benzalkonium chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In certain preferred embodiments, the surfactant comprises a pharmaceutically acceptable hydrophilic surfactant, e.g., a non-ionic surfactant. The non-ionic surfactant is preferably included in an amount sufficient to inhibit precipitation of drug substance from the pharmaceutically acceptable medium for injection (e.g., aqueous solution) after dilution. Non-ionic surfactants form stable micelles with drug substance, can solubilize the drug and may impart additional photo stability to the drug.

Using HLB values as a rough guide, hydrophilic surfactants are considered those compounds having an HLB value greater than 10 particularly from 12 to 17. The hydrophilic non-ionic surfactant is more soluble in water than in oil (having HLB higher than 10). Pharmaceutically acceptable non-ionic surfactants useful in the formulations of the present invention include but are not limited to, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters. Further examples are reaction products of a natural or polyethoxylated castor oil and ethylene oxide. The ethoxylated castor oil may have an ethylene oxide content of 25 to 100 moles ethylene oxide per molecule, preferably 35 to 60 moles ethylene oxide per molecule. The natural or polyethoxylated castor oil may be reacted with ethylene oxide in a molar ratio of from about 1:35 to about 1:60, with optional removal of the polyethoxylated component from the products. Non-ionic hydrophilic surfactants useful in the present invention further include alkylgluceosides; alkylmaltosides; alkylthioglucosides; lauryl macrogolglycenides; polyoxyethylene alkyl ethers; polyoxyethylene alkylphenols; polyethylene glycol fatty (mono- and di-) acid esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene sterols and analogues thereof; polyoxyethylene vegetable oils; polyoxyethylene hydrogenated vegetable oils; reaction mixtures of polyols and at least one member selected from the group consisting of fatty acids, glycerides, vegetable oils, hydrogenated vegetable oils, in sterols; sugar esters, sugar ethers; sucroglycerides; fatty acid salts, bile salts, phospholipids, phosphoric acid esters, carboxylates, sulfates, sulfonates. More specifically, the nonionic surfactant may comprise, for example, polyoxyethylene fatty alcohol esters, sorbitan fatty acid esters (Spans), polyoxyethylene sorbitan fatty acid esters (e.g., polyoxyethylene (20) sorbitan monooleate (Tween® 80), polyoxyethylene (20) sorbitan monostearate (Tween® 60), polyoxyethylene (20) sorbitan monolaurate (Tween® 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremophor® A25, Cremophor® A20, Cremophor® EL) and other Cremophors®, sulfosuccinates, alkyl sulphates (SLS); PEG glyceryl fatty acid esters such as PEG-8 glyceryl caprylate/caprate (Labrasol®), PEG-4 glyceryl caprylate/caprate (Labrafac® Hydro WL 1219), PEG-32 glyceryl laurate (Gelucire® 444/14), PEG-6 glyceryl mono oleate (Labrafil® M 1944 CS), PEG-6 glyceryl linoleate (Labrafil® M 2125 CS); propylene glycol mono- and di-fatty acid esters, such as propylene glycol laurate, propylene glycol caprylate/caprate; polyoxyethylene (100) stearyl ether (Brij® 700), ascorbyl-6-palmitate, stearylamine, sodium lauryl sulfate, polyoxethyleneglycerol triiricinoleate, and any combinations or mixtures thereof. Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful. Examples of the same include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Polyethylene glycol fatty acid esters are also suitable for use as surfactants in the compositions of the present invention, such as PEG-20 dilaurate, PEG-20 dioleate, PEG-20 distearate, PEG-32 dilaurate, PEG-32 dioleate, PEG-20 glyceryl laurate, PEG-30 glyceryl laurate, PEG-40 glyceryl laurate, PEG-20 glyceryl oleate, and PEG-30 glyceryl oleate. The hydrophilic surfactant may further comprise mixtures of any of the foregoing.

Polysorbate 80, an especially preferred hydrophilic non-ionic surfactant in the formulations of the present invention, is a surfactant commonly used in protein parenteral formulations to minimize denaturation at the air—water interface. Polysorbate 80 is also sometimes used in injectable solution formulations of small molecules for the purpose of solubility enhancement due to micelle formation. Polysorbates are nonionic surfactants of sorbitan esters. Polysorbates useful in the present invention include, but are not limited to polysorbate 20, polysorbate 40, polysorbate 60, polysorbate 80 (Tween® 80) and any combinations or mixtures thereof. Other suitable preferred surfactants include poloxamer, poloxamer 407, and Transcutol®. The surfactant can be any surfactant suitable for use in pharmaceutical compositions. Suitable surfactants can also be ionic hydrophilic surfactants or hydrophobic surfactants. Suitable hydrophilic surfactants can be anionic, cationic, zwitterionic or non-ionic, although non-ionic hydrophilic surfactants are presently preferred.

In certain embodiments, the concentration of the chemotherapeutic agent(s) in the pharmaceutically acceptable solvent (carrier) for injection is from about 1 mg/1 ml to about 50 mg/ml. In certain preferred embodiments, the concentration of the chemotherapeutic agent(s) in the pharmaceutically acceptable solvent (carrier) for injection is from about 10 mg/5 ml to about 500 mg/5 ml.

In certain embodiments, the injectable formulation may include a buffer. The buffer is used in an appropriate amount to adjust the pH of the formulation to an injectable range, for example about pH 6 to about pH 8 and preferably about pH 7. The buffer may be, for example, sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine, and citric acid. The injectable formulation may contain two or more buffers.

In certain embodiments, the injectable formulation may include an isotonic agent to adjust the osmotic pressure of the present formulation to an injectable range. The isotonic agent may be, for example, sodium chloride, and D-mannitol. Preferably, the isotonic agent is sodium chloride.

In certain preferred embodiments, the pharmaceutically acceptable carrier for the chemotherapeutic agent comprises water (e.g., an aqueous carrier). The term "water" used herein is defined as purified water, or the same or a higher grade thereof; and such water needs to be sterilized after dissolving various ingredients therein, or already-sterilized water (e.g. water for injection) is used in the process which is carried out under sterile condition throughout the steps. In addition, the term "water for injection" used herein includes water sterilized through a sterile filter etc. after dissolving substrates or reagents into the above-mentioned "water" (as a starting material).

In certain embodiments of the present invention, the injectable formulation of the present invention is premixed and stored in a pharmaceutically acceptable container (e.g., a vial) for later use. In such embodiments, it is preferable that the injectable formulation is one that provides adequate stability in accordance with guidelines provided, e.g., by governmental regulatory authorities such as the United States Food and Drug Administration ("FDA"). In other embodiments, it is contemplated that the chemotherapeutic agent will be separately supplied and mixed together with inactive pharmaceutically acceptable ingredients such as those described herein within a short time or immediately prior to being injected into the tumor of e.g., a human patient. In such embodiments, the chemotherapeutic agent (e.g., a taxane) may be stored in one container and a pharmaceutically acceptable carrier for injection stored in another container, the pharmaceutically acceptable carrier being an aqueous liquid or organic liquid. After mixing the contents of the two containers, a pharmaceutically acceptable injectable formulation is preferably formed, which in certain embodiments may be a suspension and may provide a sustained release of the chemotherapeutic agent. The injectable formulation of the invention can be administered through the following steps; i.e., from a vial filled with the present formulation, the content is transferred into an injection syringe via a needle and then administered directly into a tumor(s).

Furthermore, in certain embodiments, the present formulation may comprise one container such as a vial containing crystallized or lyophilized chemotherapeutic agent or the crystal of the chemotherapeutic agent may be isolated, dried, and then put into a container such as a vial to give a powder-filled formulation. The lyophilize formulation or the powder-filled formulation can be administered by mixing the contents of that vial with a second vial that contains the pharmaceutically acceptable excipients needed to deliver the chemotherapeutic agent to the tumor. For example, the second vial may comprise an injectable solution or suspension for the chemotherapeutic agent and the final formulation is prepared by mixing the chemotherapeutic agent of the first vial with the injectable suspension of the second vial just before use. Further, the injectable suspension or solution of the second container may be sterilized and/or ultrasonicated and/or sterilized by filtration for instance and then filled in a vial. The particles of the chemotherapeutic agent can be filled into vials and then sterilized by gamma-irradiation. The chemotherapeutic particles and the suspension (or solution) medium may be extemporaneously mixed so as to suspend or dissolve the chemotherapeutic particles in the vehicle for injection before administration.

The injectable formulation according to the present invention may be useful for administration with a sustained-release of the chemotherapeutic agent for at least 3 hours, or for at least 4 hours, 5 hours, 6 hours, 12 hours, 24 hours, 30 hours, 36 hours, 48 hours or more.

DETAILED DESCRIPTION OF THE PREFERRED EMBODIMENTS

The following examples of anticancer formulations in accordance with the present invention are not to be construed as limiting the present invention in any manner and are only examples of the various formulations described herein. It is contemplated that injectable formulations of the invention as described below can be made at about the time the patient is to be treated, for example, one vial may contain the chemotherapeutic agent (e.g., paclitaxel) and another vial may contain the solvent and any other optional pharmaceutical excipients suitable for injection, and these materials may then be mixed prior to direct injection into a tumor in the patient as described herein. Alternatively, it is also contemplated that the method of manufacture described herein may be used to prepare a premixed injectable formulation (preferably stable as defined herein) and that this injectable formulation is then stored in a pharmaceutically acceptable container(s) (e.g., vial) under acceptable storage conditions for later use. Scale-up of the methods of manufacture set forth below is also contemplated.

Example 1—Paclitaxel with PEG 300

400 ml of PEG 300 was placed into a beaker at 25° C., and then the liquid was heated to 85-95° C. 4.5 grams of anhydrous paclitaxel was then added to the beaker with mixing (the contents of the beaker under shearing conditions). An additional amount of PEG 300 was added to the beaker until the volume reached 450 ml. The resultant solution was passed through a 0.22-micron filter while applying nitrogen, then 3 ml of filtrate was filled into a vial and sealed. The paclitaxel solution was colorless, transparent with pH value of 7.96 after it was prepared. The content and impurity of the paclitaxel solution I provided in Table 7.

TABLE 7

| | Assay % | Baccatin III | Ethyl Ester side chain | 10-deacetyl paclitaxel | 10-Deacetyl-7-epipaclitaxel criteria | 7-Epi paclitaxel | Other largest Impurity | Total Impurity |
|---|---|---|---|---|---|---|---|---|
| TEMP/D | 90.0~110.0 | ≤0.8 | ≤0.4 | ≤0.8 | ≤0.5 | ≤0.6 | ≤0.1 | ≤2.0 |
| RT/0 D | 97.2 | 0.06 | ND | 0.03 | 0.03 | 0.03 | 0.04 | 0.25 |
| 5° C./7 D | 97.8 | 0.06 | ND | 0.03 | 0.03 | 0.03 | 0.08 | 0.31 |
| 5° C./14 D | 97.9 | 0.07 | ND | 0.03 | 0.03 | 0.04 | 0.04 | 0.26 |
| 5° C./1 M | 98.7 | 0.06 | ND | 0.03 | 0.03 | 0.03 | 0.08 | 0.35 |
| 5° C./2 M | 97.6 | 0.06 | ND | 0.02 | 0.03 | 0.03 | 0.04 | 0.26 |
| 5° C./3 M | 98.2 | 0.06 | ND | 0.03 | 0.03 | 0.03 | 0.03 | 0.25 |
| 5° C./6 M | 97.6 | 0.06 | ND | 0.03 | 0.03 | 0.02 | 0.03 | 0.20 |
| 5° C./9 M | 98.0 | 0.06 | ND | 0.02 | 0.03 | 0.02 | 0.03 | 0.20 |
| 20° C./7 D | 97.4 | 0.06 | ND | 0.03 | 0.03 | 0.03 | 0.05 | 0.29 |
| 20° C./14 D | 97.8 | 0.07 | ND | 0.04 | 0.03 | 0.03 | 0.04 | 0.28 |
| 20° C./1 M | 98.6 | 0.08 | ND | 0.04 | 0.03 | 0.03 | 0.05 | 0.37 |
| 20° C./2 M | 96.9 | 0.10 | ND | 0.03 | 0.03 | 0.03 | 0.04 | 0.32 |
| 20° C./3 M | 98.4 | 0.12 | ND | 0.04 | 0.03 | 0.03 | 0.05 | 0.36 |
| 20° C./6 M | 98.7 | 0.16 | ND | 0.05 | 0.03 | 0.03 | 0.07 | 0.39 |
| 20° C./9 M | 97.9 | 0.19 | ND | 0.06 | 0.03 | 0.03 | 0.09 | 0.46 |
| 40° C./7 D | 98.0 | 0.14 | ND | 0.04 | 0.03 | 0.04 | 0.07 | 0.43 |
| 40° C./14 D | 97.4 | 0.24 | ND | 0.06 | 0.03 | 0.06 | 0.12 | 0.58 |
| 40° C./1 M | 97.8 | 0.34 | ND | 0.07 | 0.03 | 0.07 | 0.20 | 0.99 |
| 40° C./2 M | 96.5 | 0.55 | ND | 0.12 | 0.03 | 0.11 | 0.33 | 1.33 |
| 40° C./3 M | 96.1 | 0.71 | ND | 0.14 | 0.03 | 0.13 | 0.44 | 1.62 |
| 40° C./6 M | 94.0 | 1.09 | ND | 0.19 | 0.03 | 0.21 | 0.69 | 2.40 |
| 40° C./9 M | 94.6 | 1.44 | ND | 0.27 | 0.03 | 0.28 | 0.90 | 3.29 |

Specifications: 3 mL: 30 mg paclitaxel, Inactive PI: PEG300

RESULTS: The impurity of the batch was stable at 5° C. and 20° C., but unstable at 40° C.

Example 2—Paclitaxel with Soybean Oil 730 ml of soybean oil was placed into a beaker at 25° C., and the liquid was then heated to 85-95° C. 4.5 grams of anhydrous paclitaxel was then added to the beaker with mixing (the contents of the beaker under shearing conditions). As the anhydrous paclitaxel was not dissolved, 300 ml of dehydrated ethanol was added to the beaker to dissolve the paclitaxel. The resultant solution was maintained at 70-80° C. to evaporate the ethanol. An additional amount of soybean oil was added to the beaker until the volume reached 750 ml. The resultant solution was passed through a 0.22-micron filter while applying nitrogen, then 5 ml of filtrate was filled into a vial and sealed.

The paclitaxel solution was pale yellowish, transparent with pH value of 7.63 after it was prepared. The content and impurity of the paclitaxel solution under various storage conditions is shown in Table 8.

TABLE 8

| | Assay % | Baccatin III | Ethyl Ester side chain | 10-deacetyl paclitaxel | 10-Deacetyl-7-epipaclitaxel criteria | 7-epipaclitaxel | Other largest Impurity | Total Impurity |
|---|---|---|---|---|---|---|---|---|
| temp./d | 90.0~110.0 | ≤0.8 | ≤0.4 | ≤0.8 | ≤0.5 | ≤0.6 | ≤0.1 | ≤2.0 |
| RT/0 D | 96.9 | 0.06 | ND | 0.04 | 0.03 | 0.19 | 0.18 | 0.70 |
| 5° C./7 D | 101.3 | 0.04 | ND | 0.03 | 0.03 | 0.14 | 0.05 | 0.53 |
| 20° C./7 D | 103.5 | 0.04 | ND | 0.03 | 0.03 | 0.14 | 0.06 | 0.58 |
| 40° C./7 D | 96.8 | 0.04 | ND | 0.03 | 0.03 | 0.14 | 0.07 | 0.60 |

Specifications: 5 mL: 30 mg, inactive PI: soybean oil

RESULTS: The samples at 5° C. and 20° C. were clear and transparent, and the samples at 40° C. had obvious flocs, which might be paclitaxel precipitation.

Example 3—Paclitaxel in 75% Ethanol 150 ml of dehydrated ethanol was placed into a beaker at 25° C., and then 1.2 gram of anhydrous paclitaxel was added to the beaker with mixing (the contents of the beaker under shearing conditions). An additional amount of water for injection(sterile) was added to the beaker until the volume reached 200 ml. The resultant solution was passed through a 0.22-micron filter while applying nitrogen, then 5 ml of filtrate was filled into a vial and sealed. The paclitaxel solution was colorless, transparent with pH value of 7.97 after it was prepared. The content and impurity of the paclitaxel solution under various storage conditions is shown in Table 9.

TABLE 9

|  | Assay % | Baccatin III | Ethyl Ester side chain | 10-deacetyl paclitaxel | 10-Deacetyl-7-epipaclitaxel criteria | 7-Epipaclitaxel | Other largest Impurity | Total Impurity |
| --- | --- | --- | --- | --- | --- | --- | --- | --- |
| TEMP/D | 90.0~110.0 | ≤0.8 | ≤0.4 | ≤0.8 | ≤0.5 | ≤0.6 | ≤0.1 | ≤2.0 |
| RT/0 D | 102.7 | 0.10 | 0.04 | 0.04 | 0.02 | 0.16 | 0.06 | 0.49 |
| 20° C./5 D | 102.7 | 0.23 | 0.10 | 0.08 | 0.03 | 0.39 | 0.03 | 0.92 |
| 20° C./13 D | 102.1 | 0.38 | 0.19 | 0.11 | ND | 0.60 | 0.05 | 1.33 |
| 20° C./20 D | 100.5 | 0.62 | 0.30 | 0.19 | 0.03 | 1.06 | 0.07 | 2.36 |

Specifications: 5 mL: 30 mg, Inactive PI 75% ethanol

RESULTS: With the increase of time, most impurities increased significantly, and the total impurities exceeded the standard after 20 days Example 4—Paclitaxel with Dehydrated Ethanol and Citric Acid 730 ml of dehydrated ethanol was placed into a beaker at 25° C., then 4.5 gram of paclitaxel was added to the beaker with mixing (the contents of the beaker under shearing conditions). A small amount of citric acid was added until the solution had a pH of 3.5-4.5. An additional amount of dehydrated ethanol was then added to the beaker until the volume reached 750 ml. The resultant solution was passed through a 0.22-micron filter while applying nitrogen, then 5 ml of filtrate was filled into a vial and sealed. The paclitaxel solution was colorless, transparent after it was prepared. Table 10 provides impurity data concerning the paclitaxel formulation under various storage conditions.

TABLE 10

|  | Assay % | Baccatin III | Ethyl Ester side chain | 10-deacetyl paclitaxel | 10-Deacetyl-7-pipaclitaxel criteria | 7-Epipaclitaxel | Other largest Impurity | Total Impurity |
| --- | --- | --- | --- | --- | --- | --- | --- | --- |
| TEMP/D | 90.0~110.0 | ≤0.8 | ≤0.4 | ≤0.8 | ≤0.5 | ≤0.6 | ≤0.1 | ≤2.0 |
| RT/0 D | 99.0 | 0.04 | ND | 0.03 | 0.03 | 0.04 | 0.04 | 0.25 |
| 5° C./7 D | 98.9 | 0.04 | ND | 0.03 | 0.03 | ND | 0.09 | 0.25 |
| 5° C./14 D | 98.3 | 0.05 | ND | 0.03 | 0.03 | 0.02 | 0.07 | 0.30 |
| 5° C./1 M | 99.4 | 0.04 | ND | 0.03 | 0.03 | 0.01 | 0.12 | 0.48 |
| 5° C./2 M | 101.3 | 0.04 | ND | 0.02 | 0.03 | 0.04 | 0.15 | 0.44 |
| 5° C./3 M | 100.8 | 0.04 | ND | 0.03 | 0.03 | 0.01 | 0.13 | 0.33 |
| 5° C./6 M | 99.4 | 0.03 | ND | 0.03 | 0.03 | 0.01 | 0.03 | 0.16 |
| 5° C./9 M | 100.8 | 0.03 | ND | 0.02 | 0.03 | 0.01 | 0.03 | 0.17 |
| 20° C./7 D | 97.9 | 0.04 | ND | 0.03 | 0.03 | ND | 0.05 | 0.23 |
| 20° C./14 D | 98.1 | 0.05 | ND | 0.04 | 0.03 | 0.02 | 0.04 | 0.27 |
| 20° C./1 M | 97.9 | 0.04 | ND | 0.03 | 0.03 | 0.01 | 0.17 | 0.49 |
| 20° C./2 M | 101.4 | 0.04 | ND | 0.04 | 0.03 | 0.04 | 0.08 | 0.41 |
| 20° C./3 M | 100.6 | 0.04 | ND | 0.04 | 0.03 | 0.01 | 0.06 | 0.37 |
| 20° C./6 M | 99.3 | 0.04 | ND | 0.04 | 0.03 | 0.01 | 0.03 | 0.18 |
| 20° C./9 M | 102.3 | 0.04 | ND | 0.06 | 0.03 | 0.01 | 0.03 | 0.22 |
| 40° C./7 D | 99.0 | 0.04 | ND | 0.03 | 0.03 | ND | 0.06 | 0.29 |
| 40° C./14 D | 98.3 | 0.05 | ND | 0.04 | 0.03 | 0.02 | 0.06 | 0.30 |
| 40° C./1 M | 97.5 | 0.04 | ND | 0.06 | 0.03 | 0.01 | 0.11 | 0.47 |
| 40° C./2 M | 99.4 | 0.04 | ND | 0.08 | 0.03 | 0.04 | 0.06 | 0.48 |
| 40° C./3 M | 101.7 | 0.05 | ND | 0.11 | 0.03 | 0.02 | 0.06 | 0.50 |

TABLE 10-continued

|  | Assay % | Baccatin III | Ethyl Ester side chain | 10-deacetyl paclitaxel | 10-Deacetyl-7-pipaclitaxel criteria | 7-Epipaclitaxel | Other largest Impurity | Total Impurity |
|---|---|---|---|---|---|---|---|---|
| TEMP/D | 90.0~110.0 | ≤0.8 | ≤0.4 | ≤0.8 | ≤0.5 | ≤0.6 | ≤0.1 | ≤2.0 |
| 40° C./6 M | 100.6 | 0.05 | ND | 0.15 | 0.03 | 0.02 | 0.03 | 0.38 |
| 40° C./9 M | 100.3 | 0.06 | ND | 0.24 | ND | 0.02 | 0.04 | 0.48 |

Specifications: 5 mL: 30 mg, excipients: absolute alcohol, citric acid pH 4.07

RESULTS: The impurity was stable at all temperatures, and the 10-Deacetylpaclitaxel showed an increasing trend at 40° C.

Example 5—Paclitaxel with Medium Chain Triglyceride 450 ml of Medium chain Triglyceride was placed into a beaker at 25° C., and the liquid was heated to 85-95° C. 4.5 gram of anhydrous paclitaxel was then added to the beaker with mixing (the contents of the beaker under shearing conditions). As the paclitaxel was not completely dissolved, 300 ml of dehydrated ethanol was added to the beaker to dissolve the paclitaxel. The resultant solution was maintained at 70-80° C. to evaporate the ethanol. The solution was then cooled to room temperature (25° C.). The resultant solution was passed through a 0.22-micron filter while applying nitrogen, then 3 ml of filtrate was filled into a vial and sealed. The paclitaxel solution was colorless, transparent with pH value of 5.65 after it was prepared. Table 11 provides impurity data concerning the paclitaxel formulation under various storage conditions.

RESULTS: After 6 months of storage at 20° C., the product was stable

TABLE 11

|  | Assay % | Baccatin III | Ethyl Ester side chain | 10-Deacetyl-paclitaxel | 10-Deacetyl-7-Epipaclitaxel criteria | 7-Epipaclitaxel | Other largest Impurity | Total Impurity |
|---|---|---|---|---|---|---|---|---|
| temp./d | 90.0~110.0 | ≤0.8 | ≤0.4 | ≤0.8 | ≤0.5 | ≤0.6 | ≤0.1 | ≤2.0 |
| RT/0 D | 97.4 | 0.04 | ND | 0.02 | 0.02 | 0.02 | 0.06 | 0.37 |
| 5° C./1 M | 96.9 | 0.04 | ND | 0.03 | 0.02 | 0.02 | 0.03 | 0.21 |
| 5° C./2 M | 97.2 | 0.04 | ND | 0.03 | 0.03 | 0.02 | 0.03 | 0.20 |
| 5° C./3 M | 96.8 | 0.04 | ND | 0.03 | 0.02 | 0.02 | 0.04 | 0.23 |
| 5° C./6 M | 95.7 | 0.03 | ND | 0.02 | 0.03 | 0.01 | 0.03 | 0.17 |
| 20° C./1 M | 96.9 | 0.04 | ND | 0.03 | 0.03 | 0.02 | 0.03 | 0.19 |
| 20° C./2 M | 97.5 | 0.04 | ND | 0.03 | 0.02 | 0.02 | 0.09 | 0.28 |
| 20° C./3 M | 96.8 | 0.04 | ND | 0.03 | 0.02 | 0.02 | 0.04 | 0.24 |
| 20° C./6 M | 96.8 | 0.03 | ND | 0.02 | 0.03 | 0.01 | 0.04 | 0.19 |
| 40° C./1 M | 97.1 | 0.04 | ND | 0.03 | 0.02 | 0.03 | 0.03 | 0.24 |

Specifications: 3 mL/30 mg, excipients: medium chain triglycerides

Example 6—Paclitaxel with 1,2-Propanediol 450 ml of 1,2-propanediol was placed into a beaker at 25° C., and the liquid was heated to 55-60° C. 4.5 gram of anhydrous paclitaxel was then added to the beaker with mixing (the contents of the beaker under high speed shearing). As the paclitaxel was not completely dissolved, the temperature was raised to 85-90° C., and the solution then became clear. The solution was then cooled to room temperature. The resultant solution was passed through a 0.22-micron filter while applying nitrogen, then 3 ml of filtrate was filled into the vial and sealed. The paclitaxel solution was colorless, transparent with pH value of 9.2 after it was prepared. Table 12 provides impurity data concerning the paclitaxel formulation under various storage conditions.

RESULTS: At 20° C. after 6 month storage, the product was stable.

TABLE 12

|  | Assay % | Baccatin III | Ethyl Ester side chain | 10-Deacetyl paclitaxel | 10-Deacetyl-7-Epipaclitaxel criteria | 7-Epipaclitaxel | Other largest Impurity | Total Impurity |
|---|---|---|---|---|---|---|---|---|
| temp./d | 90.0~110.0 | ≤0.8 | ≤0.4 | ≤0.8 | ≤0.5 | ≤0.6 | ≤0.1 | ≤2.0 |
| RT/0 D | 98.0 | 0.22 | 0.11 | 0.07 | 0.03 | 0.02 | 0.06 | 0.37 |
| 5° C./1 M | 96.7 | 0.05 | 0.01 | 0.03 | 0.03 | 0.03 | 0.10 | 0.30 |

TABLE 12-continued

|  | Assay % | Baccatin III | Ethyl Ester side chain | 10-Deacetyl paclitaxel | 10-Deacetyl-7-Epipaclitaxel criteria | 7-Epipaclitaxel | Other largest Impurity | Total Impurity |
|---|---|---|---|---|---|---|---|---|
| temp./d | 90.0~110.0 | ≤0.8 | ≤0.4 | ≤0.8 | ≤0.5 | ≤0.6 | ≤0.1 | ≤2.0 |
| 5° C./2 M | 98.7 | 0.07 | 0.02 | 0.04 | 0.02 | 0.06 | 0.04 | 0.29 |
| 5° C./3 M | 97.3 | 0.17 | 0.07 | 0.07 | 0.02 | 0.06 | 0.04 | 0.52 |
| 5° C./6 M | 96.0 | 0.05 | ND | 0.04 | 0.03 | 0.03 | 0.04 | 0.22 |
| 20° C./1 M | 96.6 | 0.10 | 0.03 | 0.05 | 0.02 | 0.05 | 0.03 | 0.33 |
| 20° C./2 M | 98.6 | 0.12 | 0.02 | 0.09 | 0.02 | 0.08 | 0.04 | 0.45 |
| 20° C./3 M | 97.1 | 0.20 | 0.07 | 0.11 | 0.02 | 0.09 | 0.04 | 0.64 |
| 20° C./6 M | 95.8 | 0.13 | ND | 0.15 | 0.03 | 0.08 | 0.05 | 0.50 |
| 40° C./1 M | 96.3 | 0.27 | 0.03 | 0.21 | 0.03 | 0.24 | 0.10 | 1.01 |
| 40° C./2 M | 96.1 | 0.61 | 0.03 | 0.59 | 0.03 | 0.65 | 0.25 | 2.46 |
| 40° C./3 M | 94.7 | 0.94 | 0.07 | 0.87 | 0.04 | 0.94 | 0.38 | 3.66 |
| 40° C./6 M | 92.4 | 1.23 | ND | 1.23 | 0.07 | 1.30 | 0.57 | 5.05 |

Specifications: 3 mL: 30 mg excipients: 1,2-propanediol

Example 7—Docetaxel with 75% Ethanol 150 ml of dehydrated ethanol was placed into a beaker at 25° C., then 0.8 gram of anhydrous docetaxel was added to the beaker with mixing (the contents of the beaker under shearing conditions). An additional amount of water for injection was added to the beaker until the volume reached 200 ml. The resultant solution was passed through a 0.22-micron filter while applying nitrogen, then 5 ml of filtrate was filled into a vial and sealed. The docetaxel solution was colorless, transparent with pH value of 5.0 after it was prepared. Table 13 provides impurity data concerning the docetaxel formulation under various storage conditions.

TABLE 13

|  | Impurity A | Impurity B | Impurity C | Impurity D | Other largest Impurity | Other total Impurity | Total Impurity | Assay |
|---|---|---|---|---|---|---|---|---|
| Acceptance criteria | 0.50% | 1.5% | 1.0% | 0.50% | 0.20% | — | 3.5% | 95.0%~105.0% |
| RT/0 D | 0.02% | 0.00% | 0.43% | 0.00% | 0.03% | 0.09% | 0.54% | 106.2% |
| 5° C./1 M | 0.01% | 0.02% | 1.47% | 0.05% | 0.07% | 0.16% | 1.71% | 103.8% |
| 5° C./2 M | 0.01% | 0.01% | 4.05% | 0.11% | 0.50% | 0.51% | 4.69% | 101.7% |

Specifications: 5 mL: 20 mg, IPI: 75% ethanol.

RESULTS: The formulation was unstable.

Example 8 Docetaxel with Dehydrated Ethanol and Citric Acid 400 ml of dehydrated ethanol was poured into a beaker at 25° C., and then 1.6 gram of anhydrous docetaxel was added to the beaker with mixing. The liquid was stirred. A small amount of citric acid was added until the solution had a pH of 3.5-4.5. The resultant solution was passed through a 0.22-micron filter while applying nitrogen, then 5 ml of filtrate was filled into a vial and sealed. The docetaxel solution was colorless and transparent. Table 14 provides impurity data concerning the docetaxel formulation under various storage conditions.

TABLE 14

|  | Impurity A | Impurity B | Impurity C | Impurity D | Other largest Impurity | Other total Impurity | Total Impurity | Assay |
|---|---|---|---|---|---|---|---|---|
| Acceptance criteria | 0.50% | 1.5% | 1.0% | 0.50% | 0.20% | — | 3.5% | 95.0%~105.0% |
| RT/0 D | 0.00% | 0.04% | 0.00% | 0.00% | 0.03% | 0.07% | 0.11% | 103.2% |
| 5° C./14 D | 0.02% | 0.03% | 0.04% | 0.02% | 0.02% | 0.11% | 0.22% | 102.1% |
| 5° C./1 M | 0.00% | 0.04% | 0.00% | 0.00% | 0.03% | 0.06% | 0.10% | 101.9% |
| 5° C./2 M | 0.01% | 0.04% | 0.03% | 0.00% | 0.02% | 0.02% | 0.10% | 101.1% |
| 5° C./3 M | 0.01% | 0.06% | 0.03% | 0.00% | 0.02% | 0.04% | 0.14% | 103.8% |
| 5° C./6 M | 0.00% | 0.03% | 0.00% | 0.00% | 0.15% | 0.64% | 0.67% | 100.2% |
| 25° C./14 D | 0.02% | 0.03% | 0.02% | 0.00% | 0.03% | 0.11% | 0.18% | — |
| 25° C./1 M | 0.00% | 0.03% | 0.00% | 0.00% | 0.02% | 0.04% | 0.07% | 103.6% |

TABLE 14-continued

|  | Impurity A | Impurity B | Impurity C | Impurity D | Other largest Impurity | Other total Impurity | Total Impurity | Assay |
|---|---|---|---|---|---|---|---|---|
|  |  |  |  | Acceptance criteria |  |  |  |  |
|  | 0.50% | 1.5% | 1.0% | 0.50% | 0.20% | — | 3.5% | 95.0%~105.0% |
| 25° C./2 M | 0.01% | 0.05% | 0.04% | 0.00% | 0.03% | 0.03% | 0.13% | 102.7% |
| 25° C./3 M | 0.01% | 0.06% | 0.06% | 0.00% | 0.00% | 0.09% | 0.22% | 103.9% |
| 25° C./6 M | 0.00% | 0.04% | 0.08% | 0.00% | 0.14% | 0.29% | 0.41% | 101.6% |
| 40° C./14 D | 0.00% | 0.05% | 0.00% | 0.00% | 0.04% | 0.06% | 0.11% | 102.9% |
| 40° C./1 M | 0.01% | 0.04% | 0.09% | 0.00% | 0.10% | 0.14% | 0.28% | 102.8% |
| 40° C./2 M | 0.01% | 0.07% | 0.23% | 0.00% | 0.17% | 0.32% | 0.63% | 103.6% |
| 40° C./3 M | 0.00% | 0.07% | 0.32% | 0.00% | 0.18% | 0.34% | 0.73% | 103.0% |
| 40° C./6 M | 0.00% | 0.07% | 0.60% | 0.00% | 0.30% | 0.73% | 1.40% | 103.2% |

Docetaxel solution specifications: 5 mL: 20 mg, IPI: anhydrous ethanol, citric acid to adjust pH to 3.75

RESULTS: The formulation was stable at 5° C. and 25° C. degrees.

Example 9—Docetaxel with Medium Chain Triglyceride 450 ml of medium chain triglyceride was placed into a beaker at 25° C., and the liquid was heated to 85° C.-95° C. 3 grams of anhydrous docetaxel was then added to the beaker with mixing (the contents of the beaker under high speed shearing). After cooling down to room temperature (about 25° C.), the resultant solution was passed through a 0.22-micron filter while applying nitrogen, then 3 ml of filtrate was filled into the vial and sealed. The docetaxel solution was colorless and transparent with a pH value of 5.1 after it was prepared. The content of the docetaxel solution was 100.0% with total impurity undetected on day 0 of production. Table 15 provides impurity data concerning the docetaxel formulation under various storage conditions.

TABLE 15

|  | Impurity A | Impurity B | Impurity C | Impurity D | Other largest Impurity | Other total Impurity | Total Impurity | Assay |
|---|---|---|---|---|---|---|---|---|
|  |  |  |  | Acceptance criteria |  |  |  |  |
|  | 0.50% | 1.5% | 1.0% | 0.50% | 0.20% | — | 3.5% | 95.0%~105.0% |
| RT/0 D | 0.00% | 0.00% | 0.00% | 0.00% | 0.00% | 0.00% | 0.00% | 100.0% |
| 5° C./1 M | 0.00% | 0.02% | 0.00% | 0.00% | 0.02% | 0.02% | 0.04% | 100.9% |
| 5° C./2 M | 0.01% | 0.02% | 0.00% | 0.00% | 0.04% | 0.07% | 0.10% | 100.4% |
| 5° C./3 M | 0.01% | 0.05% | 0.03% | 0.00% | 0.04% | 0.09% | 0.18% | 101.2% |
| 5° C./6 M | 0.00% | 0.04% | 0.02% | 0.01% | 0.02% | 0.03% | 0.10% | 100.4% |
| 25° C./1 M | 0.00% | 0.02% | 0.00% | 0.00% | 0.02% | 0.02% | 0.04% | 100.6% |
| 25° C./2 M | 0.01% | 0.05% | 0.00% | 0.01% | 0.03% | 0.07% | 0.14% | 101.0% |
| 25° C./3 M | 0.01% | 0.07% | 0.03% | 0.02% | 0.03% | 0.11% | 0.24% | 100.9% |
| 25° C./6 M | 0.00% | 0.11% | 0.03% | 0.02% | 0.02% | 0.05% | 0.21% | 100.1% |
| 40° C./1 M | 0.00% | 0.06% | 0.00% | 0.02% | 0.04% | 0.08% | 0.16% | 100.0% |
| 40° C./2 M | 0.01% | 0.14% | 0.05% | 0.05% | 0.04% | 0.12% | 0.37% | 100.5% |
| 40° C./3 M | 0.00% | 0.09% | 0.04% | 0.00% | 0.13% | 0.17% | 0.30% | 100.4% |
| 40° C./6 M | 0.01% | 0.23% | 0.05% | 0.08% | 0.02% | 0.06% | 0.43% | 99.8% |

Specifications: 3 mL: 20 mg, IPI: mechum chain triglycerides

RESULTS: After 6 months at different temperatures, all the impurities in this formulation did not increase significantly and were relatively stable.

Example 10—Docetaxel with PEG 300

450 ml of PEG 300 was placed into a beaker at 25° C., and the liquid was heated to 85° C.-95° C. 3 grams of anhydrous docetaxel was then added to the beaker with mixing (the contents of the beaker under high speed shearing). After cooling down to room temperature (about 25° C.), the resultant solution was passed through a 0.22-micron filter while applying nitrogen, then 3 ml of filtrate was filled into the vial and sealed. The docetaxel solution was colorless, transparent with pH value of 5.4 after it was prepared. Table 16 provides impurity data concerning the docetaxel formulation under various storage conditions.

TABLE 16

| | Impurity A | Impurity B | Impurity C | Impurity D | Other largest Impurity | Other total Impurity | Total Impurity | Assay |
|---|---|---|---|---|---|---|---|---|
| Acceptance criteria | 0.50% | 1.5% | 1.0% | 0.50% | 0.20% | — | 3.5% | 95.0%~105.0% |
| RT/0 D | 0.04% | 0.06% | 0.43% | 0.00% | 0.03% | 0.12% | 0.65% | 96.8% |
| 5° C./3 W | 0.00% | 0.06% | 0.41% | 0.00% | 0.02% | 0.10% | 0.57% | 97.2% |
| 5° C./6 W | 0.02% | 0.05% | 0.45% | 0.02% | 0.03% | 0.07% | 0.61% | 97.7% |
| 5° C./2 M | 0.02% | 0.06% | 0.41% | 0.02% | 0.02% | 0.05% | 0.56% | 97.3% |
| 5° C./3 M | 0.02% | 0.07% | 0.40% | 0.00% | 0.02% | 0.05% | 0.54% | 98.5% |
| 5° C./6 M | 0.03% | 0.07% | 0.42% | 0.01% | 0.03% | 0.08% | 0.61% | 96.7% |
| 25° C./3 W | 0.00% | 0.08% | 0.41% | 0.00% | 0.05% | 0.16% | 0.65% | 97.1% |
| 25° C./6 W | 0.01% | 0.08% | 0.47% | 0.02% | 0.06% | 0.13% | 0.71% | 97.1% |
| 25° C./2 M | 0.02% | 0.12% | 0.45% | 0.01% | 0.05% | 0.10% | 0.70% | 96.9% |
| 25° C./3 M | 0.01% | 0.15% | 0.46% | 0.00% | 0.07 | 0.19% | 0.81% | 97.3% |
| 25° C./6 M | 0.02% | 0.15% | 0.50% | 0.02% | 0.13% | 0.27% | 0.96% | 96.3% |
| 40° C./2 W | 0.00% | 0.09% | 0.56% | 0.00% | 0.06% | 0.24% | 0.89% | 97.2% |
| 40° C./1 M | 0.03% | 0.10% | 0.68% | 0.02% | 0.14% | 0.34% | 1.17% | 96.8% |
| 40° C./2 M | 0.04% | 0.14% | 0.75% | 0.02% | 0.15% | 0.32% | 1.27% | 95.7% |
| 40° C./3 M | 0.03% | 0.16% | 0.87% | 0.04% | 0.22% | 0.41% | 1.51% | 95.9% |
| 40° C./6 M | 0.06% | 0.17% | 1.24% | 0.07% | 0.41% | 0.97% | 2.51% | 94.5% |

Docetaxel PEG solution specifications: 3 mL: 20 mg, IPI: PEG 300

RESULTS: At normal temperature, the formulation was stable.

Example 11—Docetaxel with Soybean Oil 450 ml of soybean oil was placed into a beaker at 25° C., and the liquid was heated to 85° C.-95° C. 3 grams of anhydrous docetaxel was then added to the beaker with mixing (the contents of the beaker under high speed shearing). After cooling down to room temperature (about 25° C.), the resultant solution was passed through a 0.22-micron filter while applying nitrogen, then 3 ml of filtrate was filled into the vial and sealed. The docetaxel solution was yellowish, transparent with pH value of 5.6 after it was prepared. Table 17 provides impurity data concerning the docetaxel formulation under various storage conditions.

TABLE 17

| | Impurity A | Impurity B | Impurity C | Impurity D | Other largest Impurity | Other total Impurity | Total Impurity | Assay |
|---|---|---|---|---|---|---|---|---|
| Acceptance criteria | 0.50% | 1.5% | 1.0% | 0.50% | 0.20% | — | 3.5% | 95.0%~105.0% |
| RT/0 D | 0.00% | 0.03% | 0.05% | 0.00% | 0.06% | 0.14% | 0.22% | 98.2% |
| 5° C./3 W | 0.00% | 0.04% | 0.04% | 0.00% | 0.02% | 0.05% | 0.13% | 98.5% |
| 5° C./6 W | 0.00% | 0.01% | 0.06% | 0.00% | 0.04% | 0.05% | 0.12% | 100.0% |
| 5° C./2 M | 0.00% | 0.03% | 0.04% | 0.00% | 0.01% | 0.03% | 0.10% | 99.7% |
| 5° C./3 M | 0.00% | 0.04% | 0.06% | 0.09% | 0.02% | 0.03% | 0.22% | 98.8% |
| 5° C./6 M | 0.00% | 0.03% | 0.06% | 0.00% | 0.02% | 0.02% | 0.11% | 97.8% |
| 25° C./3 W | 0.00% | 0.03% | 0.05% | 0.00% | 0.03% | 0.05% | 0.13% | 97.4% |
| 25° C./6 W | 0.00% | 0.03% | 0.06% | 0.00% | 0.04% | 0.08% | 0.17% | 99.2% |
| 25° C./2 M | 0.00% | 0.03% | 0.03% | 0.02% | 0.01% | 0.03% | 0.11% | 99.7% |
| 25° C./3 M | 0.00% | 0.11% | 0.08% | 0.12% | 0.02% | 0.04% | 0.35% | 100.5% |
| 25° C./6 M | 0.00% | 0.08% | 0.06% | 0.05% | 0.04% | 0.06% | 0.25% | 98.1% |
| 40° C./2 W | 0.00% | 0.04% | 0.07% | 0.00% | 0.02% | 0.05% | 0.16% | 97.6% |
| 40° C./4 W | 0.00% | 0.04% | 0.06% | 0.00% | 0.05% | 0.11% | 0.21% | 98.6% |
| 40° C./2 M | 0.00% | 0.08% | 0.05% | 0.04% | 0.02% | 0.08% | 0.25% | precipitaion |
| 40° C./3 M | 0.00% | 0.14% | 0.11% | 0.19% | 0.02% | 0.04% | 0.48% | precipitaion |
| 40° C./6 M | 0.00% | 0.24% | 0.15% | 0.17% | 0.03% | 0.04% | 0.60% | precipitaion |

Docetaxel oil solution specifications: 3 mL: 20 mg, IPI: soybean oil

RESULTS: The formulation was stable below 25° C. At 40° C., there was precipitation from the second month, which might have slowed the release effect.

Example 12—Docetaxel with 1,2 Propandiol 450 ml of 1,2-propanediol was placed into a beaker at 25° C., and the liquid was heated to 85° C.-95° C. 3 grams of anhydrous docetaxel was then added to the beaker with mixing (the contents of the beaker under high speed shearing). After cooling down to room temperature (about 25° C.), the resultant solution was passed through a 0.22-micron filter while applying nitrogen, then 3 ml of filtrate was filled into the vial and sealed. The docetaxel solution was colorless and transparent with a pH value of 5.5 after it was prepared. Table 18 provides impurity data concerning the docetaxel formulation under various storage conditions.

TABLE 18

|  | Impurity A | Impurity B | Impurity C | Impurity D | Other largest Impurity | Other total Impurity | Total Impurity | Assay %~ |
|---|---|---|---|---|---|---|---|---|
|  |  |  |  | Acceptance criteria |  |  |  |  |
| TEMP/D | 0.50% | 1.5% | 1.0% | 0.50% | 0.20% | — | 3.5% | 95.0 105.0 |
| RT/0 D | 0.00% | 0.00% | 0.16% | 0.00% | 0.00% | 0.00% | 0.16% | 99.3 |
| 5° C./2 W | 0.00% | 0.03% | 0.15% | 0.00% | 0.01% | 0.03% | 0.21% | 99.5 |
| 5° C./1 M | 0.01% | 0.02% | 0.20% | 0.01% | 0.04% | 0.07% | 0.31% | 99.4 |
| 5° C./2 M | 0.02% | 0.01% | 0.41% | 0.02% | 0.04% | 0.07% | 0.53% | 99.1 |
| 5° C./3 M | 0.00% | 0.03% | 0.24% | 0.00% | 0.03% | 0.05% | 0.32% | 99.0 |
| 5° C./6 M | 0.00% | 0.00% | 0.13% | 0.00% | 0.01% | 0.07% | 0.20% | 96.5 |
| 25° C./2 W | 0.00% | 0.02% | 0.21% | 0.00% | 0.01% | 0.03% | 0.26% | 99.9 |
| 25° C./1 M | 0.00% | 0.01% | 0.36% | 0.02% | 0.04% | 0.08% | 0.47% | 99.5 |
| 25° C./2 M | 0.02% | 0.02% | 0.65% | 0.03% | 0.06% | 0.11% | 0.83% | 100.7 |
| 25° C./3 M | 0.02% | 0.04% | 0.59% | 0.02% | 0.05% | 0.08% | 0.75% | 98.0 |
| 25° C./6 M | 0.04% | 0.02% | 0.74% | 0.03% | 0.06% | 0.11% | 0.94% | 96.9 |
| 40° C./2 W | 0.00% | 0.03% | 0.64% | 0.00% | 0.04% | 0.09% | 0.76% | 98.6 |
| 40° C./1 M | 0.00% | 0.01% | 1.60% | 0.04% | 0.10% | 0.21% | 1.86% | 97.6 |

Specifications: 3 mL: 20 mg, IPI: 1,2-propanediol

RESULTS: The formulation was sensitive to temperature, and the impurities increased obviously with the increasing of storage temperature. At 40° C., the impurities and total impurities increased and the content decreased obviously. White turbidity began to appear at different temperatures after 3 months. This might be due to precipitation due to over-saturation.

Example 13—Hydroxycamptothecin with PEG300

300 ml of PEG 300 was placed into a beaker at 25° C., and the liquid was heated to 85° C.-95° C. 3 grams of hydroxycamptothecin was then added to the beaker and was dissolved (the contents of the beaker under high speed shearing). After cooling down to room temperature (about 25° C.), the resultant solution was passed through a 0.22-micron filter and 5 ml of filtrate was filled into the vial under nitrogen protection. The product was then sealed and sterilized at 121° C. for 15 minutes. The hydroxycamptothecin solution was yellowish, transparent with pH value in the range of 8.2-8.7, the content was 104.2% and the total impurity was 0.6% after it was prepared.

Example 14—Teniposide with PEG300

10 g Teniposide was added to 500 ml PEG 300 in a beaker and then heated to 100° C. Teniposide was completely dissolved under high speed shearing. After cooling down to room temperature (about 25° C.), the resultant solution was passed through a 0.22-micron filter and 5 ml of filtrate was filled into the vial under nitrogen protection. The product was then sealed sterilized at 121° C. for 15 minutes. The Teniposide solution was colorless and transparent with a pH value of 5.7. After sterilization, the content was 99.3% and the total impurity was 1.3%.

Example 15—Etoposide with PEG300

15 g Etoposide was added to 200 ml PEG 300 and then the mixture was heated to 55-65° C. Etoposide was completely dissolved by high-speed shearing. After cooling down to room temperature (about 25° C.), the resultant solution was passed through a 0.22-micron filter and 5 ml of filtrate was filled into the vial under nitrogen protection. The product was then sealed and sterilized at 121° C. for 15 minutes. The etoposide solution was colorless and transparent with a pH value of 4.5 after it was prepared. The content of the Etoposide solution was 94.5% and the total impurity was 0.8%.

After three generations of resuscitation, cells in logarithmic growth phase were digested and suspended in complete medium. The number of cells was calculated, with the number of cells expected to be over 3×107/ml. The right axillary part of nude mice was disinfected by alcohol. The cell suspension was injected subcutaneously with a dose of 0.15 ml. After injection, a round translucent liquid bubble bulged up. The state of the nude mice and the growth of tumors were observed every day after injection. The success of the nude mice model of subcutaneous transplantation of tumors was judged by the criteria of subcutaneous growth of palpable tumors with a diameter greater than 5 mm There were 45 mice with successful tumor model build up. All of the mice were 5 week old females, and had a bodyweight of 16-22 g. The successful nude mice were randomly divided into four groups: 11 in the positive control group, 11 in the high dose group, 11 in the low dose group and 12 in the negative control group. After grouping, intravenous injection was administered in the positive control group, with the other groups administered different tested product or blank solvent by intratumoral injection. Table 19 below provides information concerning the etoposide injection and the regimen used. Table 20 provides the average tumor volume in the nude mice before and after injection of etoposide.

TABLE 19

Etoposide injection used regimen

| Groups | Positive control | High dose | Low dose | Negative control |
|---|---|---|---|---|
| Drug injection route | Causal Vein I.V. | intratumoral | intratumoral | intratumoral |
| Dosage & method of use: On the 1st day | 100 ul: 70 ug | 5 ul:140 ug | 5 ul: 35 ug | Blank solvent, 5 ul PEG 300 |
| $2^{nd}$ week: for 5 consecutive days | 100 ul containing 550 ug | 25 ul containing 1100 ug | 12 ul containing 550 ug | 25 ul peg 300 |
| Dosage in kg | 27.5 mg/kg | 55 mg/kg | 27.5 mg/kg | / |
| Ratio of tested dosage to LD50 | 27.5/15 = 183% | 55/15 = 366% | 27.5/15 = 183% | / |

Intravenous LD50 of the mice: 15 mg/kg

TABLE 20

Average Tumor Volume in nude mice before and after injection of etoposide

| group | V0 | V3 | V6 | V9 | V11 | V12 | V15 | V18 | 6 days after injection % | 12 days after injection % |
|---|---|---|---|---|---|---|---|---|---|---|
| I.V control | 172.9 | 261.3 | 320.4 | 398.9 | 390.8 | 230.2 | / | | $PV_6/NV_6$ = 79.4 | $PV_{12}/NV$ = 31.7 |
| High dosage | 174.4 | 268.5 | 364.2 | 472.5 | 384.0 | 276.3 | / | | $HV_6/NV_6$ = 90.2 | $HV_{12}/NV$ = 38.0 |
| Low dosage | 173.0 | 246.5 | 331.2 | 416.4 | 400.7 | 358.1 | 474.1 | 678.1 | $LV_6/NV_6$ = 82.1 | $LV_{12}/NV$ = 49.3 |
| Negative peg 300 | 170.8 | 249.0 | 403.6 | 651.5 | 707.0 | 726.3 | 1010.1 | 1417. | | |

The longest diameter a (mm) and the shortest diameter b (mm) of tumors were measured by electronic Vernier caliper. The tumor volume of nude mice was calculated by formula: $TV=ab^2/2$, and the relative tumor volume (RTV) was acquired as RTV=V t/Vo. Vo was the volume of tumors before injection and V t was used to measure the volume of tumors some days after first injection. The volume of the tumor of the positive group was small because the appetite of the mice in this intravenous injection group was decreased due to severe adverse reaction. Twelve (12) days after injection, LV12/NV=49.3%, showing the effect of inhibition of the growth of tumor. Table 21 provides the survival time of each group of tested mice after drug administration. All the mice of the negative control group were alive 20 days after injection. The volume of the tumor of all the mice of the negative group was greater than 1500 mm3. The mice were killed 21 days after injection for ethical reasons. Of note, three of the mice of the low dosage group survived for 20 days after injection. Table 22 provides a comparison of median survival time and 30% survival time of high and low dose groups compared to a positive control group of etoposide.

TABLE 21

Survival time of each group after drug administration

| | Day | | | | | | | |
|---|---|---|---|---|---|---|---|---|
| group | 0 | 6 | 9 | 11 | 12 | 15 | 18 | 19 | 20 |
| IV. | 11 | 11 | 9 | 2 | 0 | | | | |
| High dosage | 11 | 11 | 11 | 11 | 2 | 0 | | | |
| Low dosage | 11 | 11 | 11 | 11 | 11 | 6 | 4 | 3 | 3 |
| Negative | 12 | 12 | 11 | 11 | 11 | 10 | 10 | 10 | 10 |

TABLE 22

Comparison of median survival time and 30% survival time of high and low dose groups compared to a positive control group of etoposide

| TG/PCG | MST | 30% ST |
|---|---|---|
| HDG/PCG | 122% (11/9 = 1.22) | / |
| LDG/PCG | 167%(15/9 = 1.67) | 200% (18/9 = 2) |

For volume of the other Groups, the local injection obtained a better result than the negative control injection. Although the apparent result was not better than intravenous injection, this was due to the toxic effect of the large dosage intravenous injection of etoposide which reduced the appetite of the mice. For survival time of the mice, the MST of the low dosage group was 15 days, the MST of the intravenous group was 9 days. The ratio of MST of the two groups was 1.67($^{15}$/$_9$=167%) and was above the criteria of 125%. Intravenous injection of a large dosage of etoposide had a poor result when compared to the negative group. Although the mice of the negative group were expected to die after 21 days, three of the mice in the low dosage group were still alive 21 days after first injection. The overall survival of the mice receiving local intratumor injection of low dosage of etoposide was longer than the survival of the negative group. Therefore, local intratumor injection of low dosage group was superior to the intravenous injection and the negative control group. However, results would be improved by further reduction of the dosage of the local injection.

Example 16—Intratumor Injection of Paclitaxel

In Example 16, the median survival time of the mice by intratumor injection of paclitaxel oil solution versus intravenous injection of paclitaxel solution in the nude mice model of subcutaneous transplantation of liver cancer are compared in a randomized pilot study.

Methods:

Study design and implementation: A randomized in vivo antineoplastic experiment of human tumor xenograft model in nude mice was done. The animals used were healthy and all of the mice were male. The mice were all 5-6 weeks old and weighed 19-24.5 grams.

Establishment of Tumor Model in Nude Mice:

The right axilla of each nude mouse was sterilized by alcohol. Liver cancer cell(Hepg2) suspension was injected subcutaneously with a dosage of 0.15 mL per dose. The concentration of the cancer cell was $3*10^7$/mL. The suspension was injected slowly and after injection, a round translucent bubble was formed. The health of the nude mice and the volume of the tumors were observed every day after injection, and the nude mice with the largest and smallest diameter of tumors was measured every 3 days. The nude mice model of subcutaneous transplantation of tumors was established when the volume of the tumor reached about 50 mm³.

Random grouping and administration of drugs to the experimental animals was completed 2 weeks later. The tumors of the nude mice grew to about 250 mm³ in volume. Fifty nude mice were randomly assigned into five groups of 10 mice each. Group 1 was a negative control group, Group 2 was a high-dose group, Group 3 was middle dose group, Group 4 was a low-dose group and Group 5 was a positive control group. After grouping, the tumor of the mouse of Group 1 was injected directly with blank solvent (8 μL of median chain oil) once every 3 weeks of the experiment or until the size of the tumor reached 2000 mm³ in volume. Due to animal ethics, the mice were executed and the experiment terminated when the volume of their tumors was larger than 2,000 mm³. The tumors of the mice of other 3 groups (Groups 2, 3 and 4) were injected directly with paclitaxel oil solution once every 3 weeks of the experiment. The tumor of each mouse of Group 2 was injected directly with 32 μL of paclitaxel oil solution containing 480 μg of paclitaxel (2 times the amount of intravenous injection of paclitaxel of LD50 of the mice). The tumor of each mouse of Group 3 was injected directly with 16 μL of paclitaxel oil solution containing 240 μg of paclitaxel (the same amount as I.V. LD50 of the mice. The tumor of each mouse of Group 4 was injected directly with 8 μL of paclitaxel oil solution containing 120 μg of paclitaxel (½ the amount of I.V. LD50 of the mice). For Group 5, (the positive control group), each mouse was injected with 100 μL of paclitaxel solution containing 120 μg paclitaxel in the caudal vein of the mouse. The mice of Groups 2, 3 and 4 were not executed when the tumors reached 2000 mm³ in volume, because the volume of the increasing tumor might have been due to a toxic effect of the paclitaxel which needed to be evaluated and also because the mice were under treatment. Table 23 provides information concerning the grouping and administration of the drug in the mice.

TABLE 23

Grouping randomly and administration of drugs in experimental animals

| group | Blank model | High dosage | Middle dosage | Low dosage | Positive control |
|---|---|---|---|---|---|
| Route of administration | | Local injection of tumor | | | Caudal vein injection |
| Drug used & Dosage | Blank Solvent: 8 ul median chain oil | 480 μg/32 ul | 240 μg/16 ul paclitaxel oil solution | 120 μg/8 ul | 120 μg/100 ul paclitaxel solution |

The intravenous LD50 of the mice was 12 mg/kg. The average weight of the mice was was 20 g, and therefore 120 μg was half the amount of LD50 of the mice. This amount, 6 mg per kg of the mouse, was larger than the amount that would be injected in a human patient. The dosage for a human patient is 1.73*135 mg/m2=233.5 mg. The dosage of human body was divided by 60 kg, which is 3.9 mg/kg.

The mice of the negative control group (tumor only injected with median chain oil) was compared with the 4 tested groups for the volume of the tumor, mortality, survival time, body weight. The mice of the Group 5 (the positive control group having drug injected into the caudal vein of the mice) were compared with the 3 drug tested groups for the volume of the tumor, mortality, survival time and body weight. For the mice in Groups 2, 3, 4 and 5, after the mouse was dead, the tumor of dead mice was examined and the concentration of paclitaxel was compared to that of mice of the other tested groups. The volume of the tumor for the mice was measured and calculated as follows: The longest diameter a (mm) and the shortest diameter b (mm) of tumors were measured by electronic Vernier caliper. The relative tumor volume (RTV) was Vt/Vo. Vo was used to represent the volume of tumor on the first day of administration of drug and Vt was used to represent the volume of tumor at a time after the first administration.

The Paclitaxel injection used in intravenous injection of mice in the positive control group consisted of paclitaxel, ethanol and polyoxyethylene castor oil. The paclitaxel oil solution for local injection contained paclitaxel and median chain oil. Each ml of injection solution contained 15 mg paclitaxel. Each bottle contained 2 ml.

Outcome:

The primary endpoint was the median survival time of the mice of each different group after injection. Secondary endpoints were the 30% survival time of the mice of each different group after first injection, the volume of the tumor after injection and the concentration of drug in the tumor.

Statistical Analysis:

This trial was designed to compare the median survival time of the mice. The percentage of increase of median survival time of each different dosage group compared to the intravenous positive control group was calculated and the evaluation criteria was when T/C % of MST is more than 125%.

Results of Groups 1, 2, 3, 4 and 5 are provided in Tables 24 and 25 below.

TABLE 24

The average volume (mm³) of tumor before and after injection of drug.

| Group | V0 | V6 | V12 | V18 | V21 | V24 | V27 | V30 | 12 days after injection | 24 days after injection |
|---|---|---|---|---|---|---|---|---|---|---|
| Positive control (PV) | 260.8 | 602 | 673 | 921 | 1161 | 1164 | 1467 | 1883 | PV/NV = 673/774 = 87% | PV/NV = 1164/1806 = 64% |
| High dosage (HV) | 263.2 | 565 | 791 | 1023 | 1100 | 1085 | 1315 | 1419 | HV/NV = 791/774 = 102% | HV/NV = 1085/1806 = 60% |
| Middle dosage (MV) | 281.2 | 577 | 781 | 1186 | 1138 | 917 | 1288 | 1298 | MV/NV = 781/774 = 100% | MV/NV = 917/1806 = 51% |
| Low dosage (LV) | 230.3 | 382 | 634 | 1053 | 1191 | 1195 | 1406 | 1286 | LV/NV = 634/774 = 81.9% | LV/NV = 1195/1806 = 66% |
| Negative (NV) | 247.5 | 521 | 774 | 1218 | 1502 | 1806 | 1581 | 1398 | When the mouse was dead, the volume of the dead mouse was not included. Therefore the figure was misleading. | |

Twenty one days after the first injection, a second dose of drug was injected into a live mouse of a different group.

TABLE 25

Relative proliferation of tumor at different times after injection

| Group Vt/V0 | RTV6 | RTV12 | RTV18 | RTV21 | RTV24 | RTV30 |
|---|---|---|---|---|---|---|
| Positive control | 2.31 | 2.58 | 3.53 | 4.45 | 4.46 | 7.22 |
| high dosage | 2.15 | 3.00 | 3.89 | 4.18 | 4.12 | 5.39 |
| middle dosage | 2.05 | 2.78 | 4.22 | 4.04 | 3.26 | 4.61 |
| low dosage | 1.66 | 2.75 | 4.57 | 5.17 | 4.54 | 5.58 |
| negative | 2.11 | 3.13 | 5.52 | 6.07 | 7.30 | 5.65 |

(RTV6, RTV12, RTV18, RTV21, RTV24 and RTV30 were relative tumor proliferation rates at 6 days, 12 days, 18 days, 21 days, 24 days and 30 days after the injection (intratumor or intravenous).

Twelve days after injection, HV>MV>NV>PV>LV but on 24 days after injection, NV>LV>PV>HV>MV. The volume of the tumor was not a sensitive indicator because the volume of the tumor depends on many factors, e.g. the appetites and the food eaten by the mouse, and the local toxic effect of anticancer drug. Also, the dosage was not individualized. Before twelve days after injection, the volume of HV and MV was bigger than LV because the local toxic effect of higher concentration of paclitaxel caused swelling of the tumor of the HV and MV groups more than that of LV group.

The median survival time of the low dosage group, the middle dosage group and high dosage group was longer than the MST of the intravenous group. The median survival time for IV group was 22 days, for high dosage group it was 27 days, for middle dosage group it was 26 days, for low dosage group it was 28 days. The relative MST of the low dosage group compared to the intravenous group PCG was 127%, which was larger than the evaluation criteria of 125%. The relative MST of the tested groups compared to the IV group (positive control group) was expressed by T/C (%).

Of the three drug tested groups having drug injected directly into the tumor, it was found that before 12 days after injection the volume of the tumor of the low dosage group was the smallest one, the relative proliferation rate of the low dosage group was also the smallest. This finding suggests that the best time to give the second injection was 1-2 weeks after the first injection. Therefore, the injection plan was changed after the second dosage. For 30% survival time, the low dosage group was the longest, at 154.2% relative to that of the IV control group, and was 142.3% relative to that of the negative control group.

The overall survival of intravenous group to negative group was about 100%, meaning that mean for liver cancer, intravenous injection was not better than palliative treatment. The FIGURE provides the survival of different mice groups over time, after the first injection of chemotherapy. Table 26 provides survival data for the test groups. At 30% survival time, the low dose group survived the longest, it was 154.2% of the IV control group, it was 142.3% of the negative control group.

TABLE 26

| ST Group | MST | T/PCG MST % | 30% ST | T/PCG 30% ST % |
|---|---|---|---|---|
| PCG | 22 | / | 24 | / |
| HDG | 27 | 122.7% | 33 | 137.5% |
| MDG | 26 | 118.2% | 32 | 133.3% |
| LDG | 28 | 127.3% | 37 | 154.2% |
| NCG | 23 | / | 26 | / |

The tumor tissue of the locally injected mouse and intravenous injected mouse was ground, and the content of paclitaxel was detected by HPLC method. For PCG, the amount of paclitaxel detected was very small and could be neglected. This confirmed that no drug was effective in curing the cancer of liver. The paclitaxel within the tumor of the middle dosage and low dosage group was about 63-66% of the dosage injected. For the high dosage group, the paclitaxel within the tumor of the mouse was about 46.7% of the dosage injected.

The above phenomenon showed that the paclitaxel oil solution had sustained released effect if injected locally. If the intravenous injection of paclitaxel is affective in curing cancer cells, then the result of local injection of anticancer drug of water insoluble property should be much better.

The experiment showed that the effect in inhibiting the growth of the tumors of the mice in the local injection group was greater than the effect in mice of intravenous injection group. It also showed that survival of the mice of intratumor injection was greater than that of intravenous injection group. The intratumor injection had a higher concentration of anticancer drug in the tumor than that of the intravenous group. This experiment showed that the best dosage should be individualized according to the size of tumor and the interval between injection should be 1-2 weeks. Table 27 provides the amount of paclitaxel in the tumors of mice of the tested and positive control groups.

TABLE 27

Amount of paclitaxel in the tumors of mice of the tested and positive control groups

| Sample No. | Mass of Tumor g | Amount of drug injected/dose μg | | | Time of death (D) | Paclitaxel detected μg | Percentage of Previous dose % | Mean % |
|---|---|---|---|---|---|---|---|---|
| | | 1st | 2nd | 3rd | | | | |
| PCG 1# | 0.5364 | 120 | / | / | 9 | 0.6 | 0.5 | 0.1 |
| PCG 6# | 1.0809 | 120 | 120 | / | 36 | 0.9 | 0.7 | |
| PCG 8# | 0.1602 | 120 | 120 | / | 29 | −0.1 | −0.1 | |
| PCG 9# | 0.3801 | 120 | / | / | 19 | −0.2 | −0.2 | |
| PCG 10# | 0.272 | 120 | / | / | 17 | −0.2 | −0.2 | |
| HDG 12# | 0.3315 | 480 | 480 | / | 28 | 158.1 | 32.9 | 46.7 |
| HDG 16# | 0.3432 | 480 | 480 | / | 34 | 349.1 | 72.7 | |
| HDG 20# | 0.4014 | 480 | 480 | / | 30 | 165.5 | 34.5 | |
| MDG 27# | 0.4096 | 240 | 240 | 240 | 37 | 158.8 | 66.2 | 66.2 |
| LDG 33# | 0.3463 | 120 | 120 | 120 | 38 | 81.6 | 68.0 | 63.0 |
| LDG 40# | 0.3309 | 120 | / | / | 19 | 69.5 | 57.9 | |

CONCLUSION

In the preceding specification, the invention has been described with reference to specific exemplary embodiments and examples thereof. It will, however, be evident that various modifications and changes may be made thereto without departing from the broader spirit and scope of the invention as set forth in the claims that follow. It will also be apparent to those skilled in the art that the local anticancer formulations of the present invention may be changed in additional ways or utilized in many additional presurgical conditions, during surgical and post-surgical treatments not specifically mentioned herein. Additionally, it is contemplated that such formulations may be utilized at additional sites not specifically mentioned herein (including topically). Such obvious modifications are considered to be within the scope of the appended claims. The specification is accordingly to be regarded in an illustrative manner rather than a restrictive sense.

What is claimed is:

1. A method of treating a malignant mass in a mammal, comprising administering an injectable formulation suitable for intratumor administration directly into the malignant mass, the injectable formulation consisting of a therapeutically effective amount of a water insoluble chemotherapeutic agent selected from a taxane, a podophyllotoxin derivative, a camptothecin derivative, and mixtures thereof dissolved or suspended in a pharmaceutically acceptable biocompatible carrier comprising a medium chain triglyceride or a pharmaceutically acceptable vegetable oil, and an optional solvent which when included consists of a non-aqueous solvent, wherein the injectable formulation is a colorless and transparent stable non-aqueous solution that does not include cholesterol, a phospholipid, a protein, or surfactant.

2. The method of claim 1, wherein the malignant mass is in a location in the mammal selected from the group consisting of brain, head, eye, nasopharynx, mouth, tongue, neck, thyroid, gastrointestinal system, liver, pancreas, gall bladder, lung, respiratory system, urogenital system, kidney, urinary bladder, breast, lymphatic system, cardiovascular system, nervous system, skin, thorax, pleural membrane, mesothelioma, lung cancer, muscular skeletal system, abdomen with primary or secondary nature.

3. The method of claim 2, wherein the malignant mass metastasized from another organ in the mammal.

4. The method of claim 2, wherein the injectable formulation is administered through a syringe or a needle of a fiberscope.

5. The method of claim 4, wherein the chemotherapeutic agent is a water insoluble compound selected from the group consisting of a taxane, a podophyllotoxin derivative, or a camptothecin derivative.

6. The method of claim 5, wherein the water insoluble compound is a taxane selected from the group consisting of paclitaxel and doxetaxel.

7. The method of claim 5, wherein the water insoluble compound is hydroxycamptothecin.

8. The method of claim 5, wherein the biocompatible carrier comprises a medium chain triglyceride and further includes a hydroalcoholic solvent.

9. The method of claim 1, wherein the chemotherapeutic agent is paclitaxel and the biocompatible carrier comprises a medium chain triglyceride.

10. The method of claim 1, wherein the malignant mass is
   (i) a superficial malignant disease of skin, eye, tongue, mouth, thyroid, breast, cervix, uterus, anus, prostate, vagina, sarcoma of the bone, carcinoma of urethra, penis, testis and epididymis and the chemotherapeutic agent is injected with a syringe directly into the malignant mass without dilution; or
   (ii) a cancer of the nasopharynx, and the chemotherapeutic agent is injected into the malignant mass with the syringe or needle through a nasopharyngoscope; or
   (iii) a cancer of the liver, kidney and gall bladder, and the chemotherapeutic agent is injected using a syringe through skin into the malignant mass with the assistance of ultrasound, or is injected through a hole made in an abdominal wall of a patient during laparoscopic surgery into the malignant mass; or
   (iv) a cancer of the ovary, oviduct, pancreas, metastasis of lymph node or direct peritoneum invasion of the abdominal cavity, lymphoma of the abdomen, and the chemotherapeutic agent is injected with the syringe into the malignant mass through a hole made in the abdominal wall of a patient during laparoscopic surgery; or
   (v) a carcinoma or sarcoma of esophagus, stomach, duodenum, small intestine, and the chemotherapeutic agent is injected with the needle into the malignant mass through an enteroscope or via a long syringe through a hole made in the abdominal wall of a patient during laparoscopic surgery or is injected through a hole made in a thoracic wall of a patient during thorascopic surgery;

(vi) a carcinoma or sarcoma of the large intestine and rectum, and the chemotherapeutic agent is injected with the needle into the malignant mass through colonoscopy or is injected using a syringe through a hole made in the abdominal wall of a patient during laparoscopic surgery; or (vii) a carcinoma or sarcoma of the lung, trachea, nasopharynx or larynx and the chemotherapeutic agent is injected into the malignant mass using the needle of a fiber bronchoscope into the malignant mass; or is injected through a hole made in the thoracic wall of a patient; or (viii) a carcinoma or sarcoma of the urinary bladder, and the chemotherapeutic agent is injected into the malignant mass with a needle through a cystoscope, or is injected through a hole made in the abdominal wall of a patient during laparoscopic surgery; or (ix) a carcinoma or sarcoma of uterus, and the injectable formulation of chemotherapeutic agent is injected into the malignant mass with a syringe or a needle of a hysteroscope; or is injected through a hole made in the abdominal wall of a patient during laparoscopic surgery; or (x) a carcinoma or sarcoma of nasopharynx and larynx, and the chemotherapeutic agent is injected into the malignant mass with a needle through a laryngoscope; or (xii) a carcinoma of the brain, and the chemotherapeutic agent is injected with a needle of a syringe or a fiberscope into the malignant mass after a hole is drilled in the corresponding bone of a skull with the use of an X-ray, CT scan or MR scan; or (xii) a malignant lymphoma or lymph node with metastasis, and the chemotherapeutic agent is injected into the malignant mass using a needle through the skin of a patient or is injected through a hole made in the abdominal wall of a patient during laparoscopic surgery or through a hole made in the thoracic wall of a patient during thoracoscopic surgery.

11. A stable intratumor injectable formulation of a water insoluble chemotherapeutic agent, consisting of a therapeutically effective amount of a chemotherapeutic agent selected from a taxane, a podophyllotoxin derivative, a camptothecin derivative, and mixtures thereof in a pharmaceutically acceptable biocompatible carrier for injection comprising a medium chain triglyceride or a pharmaceutically acceptable vegetable oil, and an optional solvent which when included consists of a non-aqueous solvent, wherein the injectable formulation is stable and suitable for intratumor administration as a solution and is a colorless and transparent non-aqueous solution that does not include cholesterol, a phospholipid, a protein, or surfactant.

12. The intratumor injection formulation of claim 11, wherein the taxane is paclitaxel.

13. The intratumor injection formulation of claim 11, wherein the chemotherapeutic agent is paclitaxel and the pharmaceutically acceptable biocompatible carrier for injection is a medium chain triglyceride is an esterification product of an acid selected from the group consisting of caproic acid, caprylic acid, capric acid, lauric acid, and mixtures thereof, further comprising a hydroalcoholic solvent.

14. The intratumor injectable formulation of claim 11, wherein the chemotherapeutic agent is hydroxycamptothecin and the pharmaceutically acceptable biocompatible carrier for injection comprises a medium chain triglyceride.

15. The intratumor injection formulation of claim 11, wherein the taxane is doxetaxel.

16. The intratumor injectable formulation of claim 11, wherein the podophyllotoxin derivative is selected from the group consisting of etoposide, teniposide, and mixtures thereof.

17. The intratumor injectable formulation of claim 11, wherein the camptothecin derivative is hydroxycamptothecin.

18. An intratumor injectable formulation kit, comprising a first vial containing a powdered water insoluble chemotherapeutic agent selected from a taxane, a podophyllotoxin derivative, a camptothecin derivative, and mixtures thereof, and a second vial containing the pharmaceutically acceptable excipients needed to deliver the chemotherapeutic agent to a tumor, the pharmaceutically acceptable excipients consisting of a pharmaceutically acceptable biocompatible carrier comprising a medium chain triglyceride or a pharmaceutically acceptable vegetable oil, and an optional solvent which when included consists of a non-aqueous solvent, wherein the injectable formulation is suitable for intratumor administration as a solution that is stable, colorless, transparent and non-aqueous and does not include cholesterol, a phospholipid, a protein, or surfactant.

19. The intratumor injectable formulation of claim 11, which further comprises a buffer to provide a pH from about 3.5 to about 4.5.

20. The intratumor injectable formulation of claim 19, wherein the buffer comprises citric acid.

21. The formulation of claim 11, wherein the injectable solution is capable of being passed through a 0.22-micron filter.

22. The formulation of claim 19, wherein the chemotherapeutic agent is paclitaxel, the pharmaceutically acceptable biocompatible carrier for injection is a medium chain triglyceride, and the solvent is dehydrated ethanol.

23. The intratumor injectable formulation of claim 18, which further comprises a buffer to provide a pH from about 3.5 to about 4.5.

* * * * *